United States Patent [19]

Adrion et al.

[11] Patent Number: 5,023,785
[45] Date of Patent: Jun. 11, 1991

[54] HEMATOLOGY - DIAGNOSIS APPARATUS EMPLOYING EXPERT SYSTEM TECHNOLOGY

[75] Inventors: Robert F. Adrion, Cary; Joan W. Curry, Durham, both of N.C.; Robert A. Levine, Guilford, Conn.

[73] Assignee: Becton & Dickinson Co., Franklin Lakes, N.J.

[21] Appl. No.: 103,935

[22] Filed: Nov. 16, 1987

[51] Int. Cl.$^5$ .............................................. G06F 15/42
[52] U.S. Cl. .............................. 364/413.08; 364/513; 138/630
[58] Field of Search ...................... 364/413.01, 413.02, 364/413.03, 413.07, 413.08, 513, 200, 900; 128/630

[56] References Cited

U.S. PATENT DOCUMENTS

| | | | |
|---|---|---|---|
| 3,686,486 | 4/1972 | Coulter et al. | 364/413.08 |
| 4,167,038 | 9/1979 | Hennessy | 364/413.08 |
| 4,199,748 | 4/1980 | Bacus | 364/413.08 |
| 4,202,033 | 5/1980 | Strobel | 364/413.08 |
| 4,290,114 | 9/1981 | Sinay | 364/900 |
| 4,315,309 | 2/1982 | Coli | 364/300 |
| 4,489,387 | 12/1984 | Lamb et al. | 364/513 |
| 4,730,259 | 3/1988 | Gallant | 364/413.02 |
| 3,731,725 | 3/1988 | Suto et al. | 364/413.01 |
| 4,733,354 | 3/1988 | Potter et al. | 364/413.02 |
| 4,763,277 | 8/1988 | Ashford et al. | 364/513 |

OTHER PUBLICATIONS

"Computer Assited Clinical Decision Making", Anthony Gorry, 1973.

Primary Examiner—Jerry Smith
Assistant Examiner—Kimthanh T. Bui
Attorney, Agent, or Firm—Carella, Byrne, Baine, Gilfillan, Cecchi & Stewart

[57] ABSTRACT

Described is a hematology-diagnosis apparatus employing expert system technology. The apparatus comprises a computer/data processor which is provided with a memory facility, a central processor and a printer. Stored in the memory facility is a knowledge base applicable to hematologic diagnostics, and instructions by which the apparatus is to process input data, in the form of a plurality of—four in a specific exemplary embodiment—hematologic parametric numerics obtained from a patient's bood assay. The numerics are entered via entry means. The apparatus accordingly executes the instructions, and on the basis of the parametric numerics, prints out diagnostic and hematologic messages applicable to the patient.

12 Claims, 2 Drawing Sheets

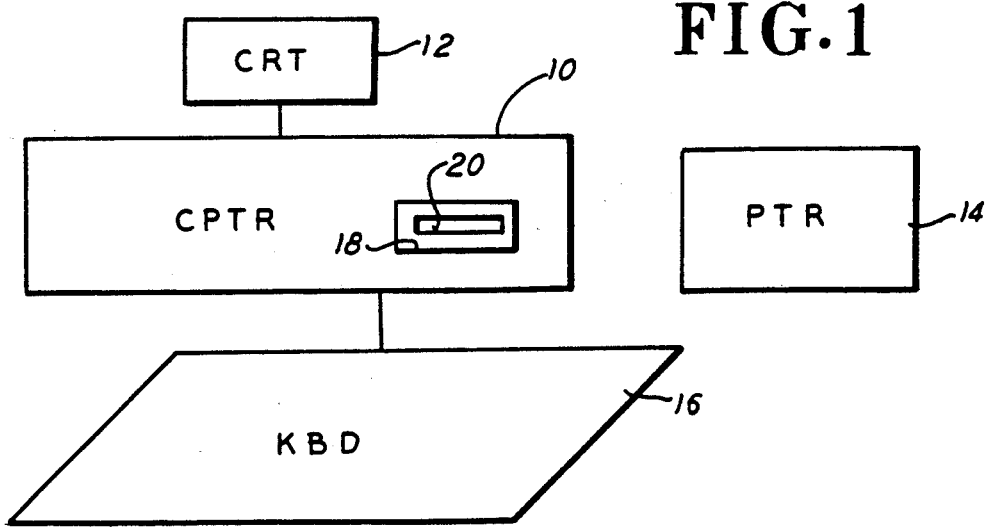
FIG. 1
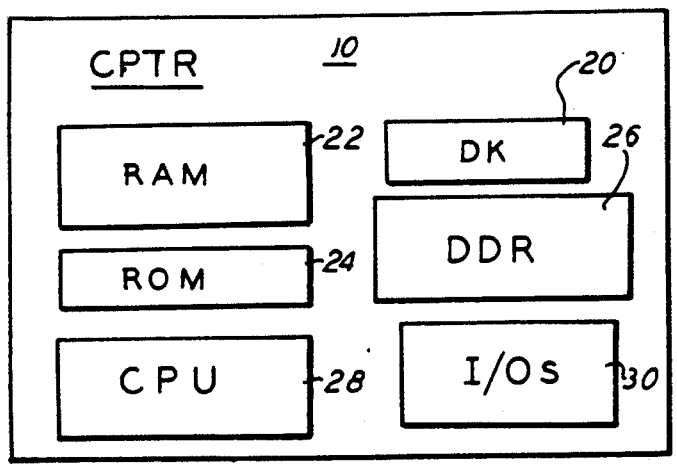
FIG. 2
FIG. 3
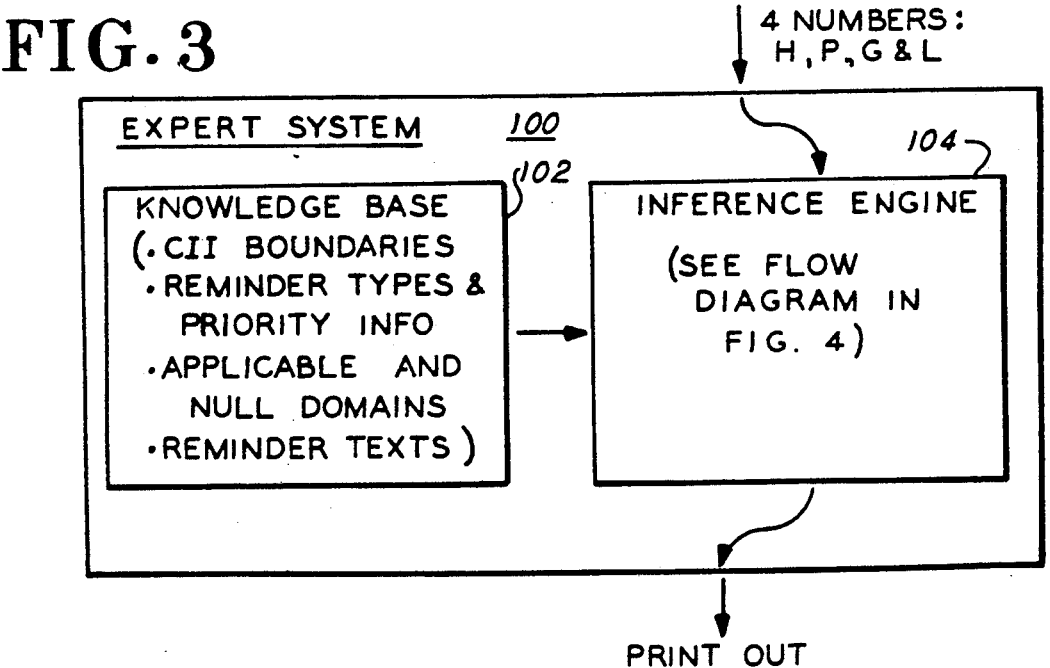

HEMATOLOGY - DIAGNOSIS APPARATUS EMPLOYING EXPERT SYSTEM TECHNOLOGY

FIELD OF THE INVENTION

This invention relates to hematology-diagnosis apparatus, that is apparatus which on the basis of instrument-obtained hematological data fed into the apparatus, retrieves from memory storage diagnostic and hematological information, and makes a record thereof available to the hematology specialist (hematologist) or even the general practitioner physician. As will be seen hereinafter the apparatus employs computer/data processor technology, and more particularly expert system technology which is a branch of the technology commonly known as artifical intelligence.

The terms "hematological" and "diagnostic" are used in broad and somewhat overlapping sense at this point; subsequently, in the description, distinction will be made between "hematological reminders" or "hematological messages", and "diagnostic reminders" or "diagnostic messages"; see for example Appendix 1 which presents some typical diagnostic printouts. Appendices will be referred to throughout this text; they are found at the end of the text. As will be seen herein seen hereinafter, at the location reserved for "diagnostic reminders" there will occasionally appear messages which decline to present a diagnosis in the truest sense of that term, or even messages termed "technical alerts" which indicate presence of actually, or possibly, invalid input data. These messages, because of their appearance at "diagnostic reminders", will be considered "diagnostic" for some purposes hereinafter. By the same taken, a message intended to appear at "hematological reminder" will be deemed to be a "hematological message", even if it seems to be somewhat of diagnostic nature.

Throughout this text references will be made to a Bibliography which appears towards the end of the Detailed Description; items are indexed there as BI 1 (read as: Bibliography. Item 1), BI 2, BI 3 etc. Throughout the description the reference will be made typically, merely as BI 1.

The hematological/medical terminology used in this text, follows rather closely the terminology presented in BI 1 and BI 9 to BI 13. The artifical intelligence/expert system terminology utilized in this text follows closely the terminology presented in BI 2, especially its Glossary; see also BI 3 to BI 6. It has been stated above, that "hematological data" are fed to the apparatus; in this text, "hematological parameters" or simply "parameters", or "hematological arguments" or simply "arguments" are used interchangeably with "hematological data". "Messages of hematology-diagnostic significance" is used occasionally as generic for "hematological" and "diagnostic" messages.

For brevity, hereinafter "apparatus of the invention", "system of the invention", will be referred respectively as "Apparatus", "System".

BACKGROUND OF THE INVENTION

Speaking as of the middle 1980s, hematological diagnostics is still practiced largely by the time-honored approach of lookup in authoritative works such as BI 1, or else the hematologist or physician depends upon his own memory. Either way, the approach is mental. As will be seen hereinafter, the hematological parameters which are processed by the Apparatus are four in number, they will be referred to throughout this description as P H G L; these are abbreviations for Platelet Count, Hematocrit, Granulocyte Count, Lymphocyte/Monocyte Count. Alternative abbreviations for these are # PLT, HCT, #GRANS, #LYMPH. The mental approach operates on the same, or similar parameters, or on parameters some of which are in the quartet just stated or similar thereto, plus other kinds of input data, e.g. patient history, clinical signs, other test results, etc. depending on the instrument-type or data source. The mental approach will now be discussed, assuming it is based on P H G L data, but the discussion is most general.

The parameters P H G L are presented to the "mental processor" (or the Apparatus) as numerics. The mental approach is by a method known in scientific or mathematical fields as trial-and-error method. On the basis of the quartet of parametric data on hand, the physician assumes that certain trial hematologic/diagnostic conditions or conclusions—plural ones (rather than just one single one) are quite common—apply to the quartet, and hence to the patient in question. Next comes lookup to see if the assumption is correct. If incorrect, another trial assumption is made, and the lookup is repeated. When eventually an assumption proves to be true or a "hit", the mental processor must continue to make trial assumptions, in order to be sure to reach all of the possibly plural "hits". For a physician who is quite experienced at this, the convergence of the process to the first correct conclusion, may be fairly rapid, because he or she will not likely assume—as an inexperienced physician might assume—a trial condition for which the given quartet of parametric numerics is far afield. Nevertheless, the trial-and-error process is too time-consuming, and is conducive to physician's diagnostic error of commission (because of fatigue, for example) and of omission (plural conclusions to be drawn).

To alleviate this situation, efforts have been made to partially automate or provide automated assistance in hematology-diagnostic processing. Before considering this, there now follows a brief review of automated systems, and in particular expert systems, directed to medical diagnostics, that is to the many fields of medicine including hematology, general medicine, and internal medicine.

The number of separate, individual, previously proposed systems directed to automated medical diagnostics is quite sizeable, but for most of these very few units were constructed. As to hematology diagnostic systems previously proposed, these are very few in number; only two have received significant publicity in the literature, and here too, for each of these two, very few units were constructed. The reasons for such limited construction, for hematology diagnostics will be presently discussed, and they apply also to general medical diagnostics.

The literature devoted to general medical diagnostic expert systems is quite extensive; BI 2 describes some and lists others in its own bibliography; indeed surveys or listings of these systems have been prepared, some with brief summaries devoted to each listed system; see BI 6 to BI 8 and BI 12.

As to hematology-diagnostic systems, their number is quite limited. One better-known system called HEME (see BI 9 to BI 12) was a computer program which used a probability approach to assist in the diagnosis of general hematologic disease. HEME was presented as a series of papers by Cornell University/International Business Machines (IBM). The development and operation of HEME spanned a time period of about 15 to 20 years. HEME was intended to operate as a continuously self-improving system. It was utilized chiefly as a research tool, and as a training device for student-hematologists. As is indicated in BI 11, pages 764, 765, HEME received little use for various reasons stated thereat.

The other better-known hematology-diagnostic system is ANEMIA which is described in BI 13. ANEMIA is an Italian-originated computer program which is designed to assist in the diagnosis of the anemia. Like HEME, ANEMIA was operated at a research center, and did not progress beyond that stage.

HEME and ANEMIA were far too complex to be used by physicians who are not also computer experts. The two systems were interactive (see BI 2), meaning that in order to develop a diagnosis, the user had to engage in a dialog with the system sequentially so and repeatedly, with the system providing questions and answers in several tiers of interrogation. Of course, interactive systems have certain advantages in certain applications, but they are not too well-suited for the small-office practitioner. As will be seen hereinafter, the System of this invention is noninteractive; the user of the System needs very few skills in operating the system which essentially takes care of itself in a "one-shot-operation".

The user of at least one of the previously proposed medical diagnostic expert systems had to be well-versed in the cryptic computer-code language, to intercommunicate both ways with the apparatus. In contrast, in the System of this invention, output information is in human language in narrative sentence form, or in the so-called short mode, in short-slogan-type word arrangements, also expressed in simple human language, and little or no human input information is required.

OBJECTS OF THE INVENTION

It is a general object of the invention to alleviate and to minimize the problems encountered in "mental processing" of hematalogical data.

It is another object of the invention to provide computer-based expert-level assistance to the physician in interpreting hematological data.

It is still another object of the invention to provide hematology-diagnosis apparatus which employs expert level hematology knowledge.

A still further object of the present invention, is to provide such hematology-diagnosis apparatus in a noninteractive arrangement which is easily operable, does not require extensive training in computer technology, and requires little or no human entry of data, and which provides readout expressed in human language.

INTRODUCTION TO THE APPROACH OF THE INVENTION

It has been stated hereinabove that the system operates on the basis of four hematological parameters HPGL, and their respective numerical input values. It should be noted that HEME (BI 9, page 588) and ANEMIA (BI13, page 17) also operated with some of the same or similar hematological parameters, but these systems used many more additional "findings" or input data; for example HEME could operate on as many as 585 findings. The System is based on operation on the basis of just a small number of parameters, and this number is kept constant. This leads to simplicity in operation, internally of this Apparatus, and also as far as the user is concerned. In the Apparatus, for each one of the four parameters, subdivision into respective ranges of its numerics is made; these ranges are termed Clinically Important Intervals or CIIs. In the System, the subdivision is made internally, and automatically. However, and as will be seen in the next Section the impact of automatic subdivision is even more dramatic. In the System, H is given twelve CIIs, P has eight, G has ten, and L has eight CIIs (see Appendix 2). The number of possibly coincidences of these four sets of CIIs—all ranges taken into account—equals $12 \times 8 \times 10 \times 8 = 7680$. However, the total number of messages (hematologic and diagnostic) is, speaking as of late 1986/early 1987 only approximately 70. By a preferred approach, discussed in the next Section, the Apparatus, instead of scanning 7680 possibilities or setting up 7680 AND conditions, scans or sets up merely the approximately 70.

Before proceeding to the next Section, it should be noted that ANEMIA (cf BI 13), and indeed most of the general medical, diagnostic systems, were so-called "rule-based" expert sytstem (cf BI 2 for explanation). Also known in the field of artificial intelligence are "frame-based" expert systems (cf. BI 3).

APPROACH OF THE INVENTION—SIMPLIFIED STATEMENT

The System has some resemblance to rule-based systems and to frame-based systems, but only insofar as the end result is concerned. The scheme of this system, in operating on the input parameters to arrive at the output printout, follows neither of these classic implementations. Briefly stated here, referring preliminarily to Appendix 5, the scheme of this System is to allocate approximately 70 positions—these are space—positions insofar as locations in memory is concerned, but also time positions, for scanning—to the approximately 70 possible hematologic and diagnostic messages, or more accurately to their respective 70 one-bit identifiers. One pre-selected bit-string or bit-stream of these positions, is formed for each one of the four parameters H P G, as represented in Appendix 5; H has twelve bit strings available, but the preselected one is predicated on the particular H input numeric or argument on hand, and similarly for P G L. Alignment, in one particular position, of all binary ones in the four bit-strings, results in "success" or "hit", and often multiple hits are achieved for the hematological messages, or the separately printed out diagnostic messages, or both. The "hit" hematological and diagnostic messages or reminders are fetched out of memory, and are printed out. The Statement of this paragraph is somewhat simplified, and will be amplified subsequently.

SUMMARY OF THE INVENTION

In accordance with the invention, the Apparatus preferably comprises a computer, which for example may be a personal computer, and as such is provided with its usual memory facilities, a central processing unit and may include peripheral devices such as a printer and viewing screen. Stored in the memory facilities is the so-called knowledge base (cf. BI2) applicable to, in the preferred embodiment, hematologic diagnostics, and instructions by which the Apparatus is to process the input data. The Apparatus also includes means for entering the input data into the Apparatus. The Apparatus accordingly executes the instructions, and preferably prints out the applicable hematological and diagnostic messages.

More detailed aspects of this summary will be presented in the subsequent description. One such aspect has been presented under the heading Approach of the Invention—Simplified Statement. That simplified statement will be amplified subsequently.

Some of the advantages of the invention have been discussed above, and others will be discussed in the Conclusion of the specification.

BRIEF DESCRIPTION OF THE DRAWINGS

Other objects, advantages, and features of the invention, as well as variations thereof, will be apparent from the following, more detailed description of which the appended claims and abstract form a part, when considered together with the accompanying drawings, in which FIG. 1 is a block diagram of computer or data processor apparatus with which the present invention may be practiced;

FIG. 2 is a block diagram of the internal structure of the computer of FIG. 1;

FIG. 3 is a block diagram of the expert system of the invention incorporable in the apparatus of FIGS. 1 and 2.

DETAILED DESCRIPTION

Introduction

Figure 4:
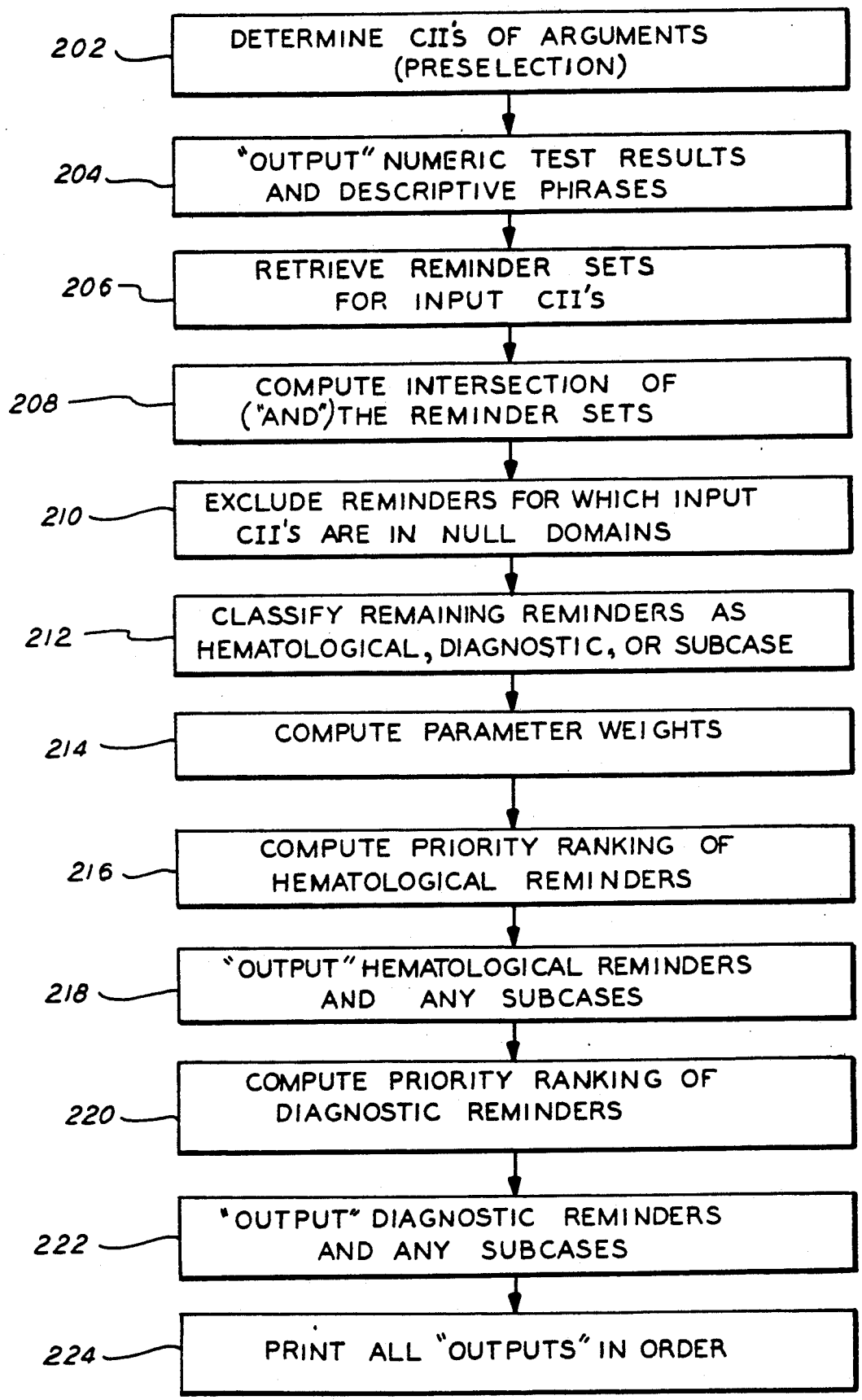
FIG. 4 is a flow diagram illustrative of the sequence of events performed by the apparatus to result in the output of the hematology diagnostics.

The invention will be described, by way of example, under the assumption that the numerics for the parameters H P G L have been obtained as measured or indicated by a hematology system manufactured by Becton Dickinson and Company, hereinafter occasionally referred to as Becton Dickinson or simply B-D, of Franklin Lakes, N.J. 07917, U.S.A., and more specifically the Clay Adams Division of that Company, also of Franklin Lakes, N.J. 07917. Becton Dickinson is the assignee of the present invention. That B-D system is known as the QBC II Centrifugal Hematological System. QBC is a Registered Trademark of Becton Dickinson and is an acronym for Quantitative Buffy Coat. The latter system will be briefly referred to as the QBC II System; it will be briefly explained here. However, it should be understood that the present invention could be practiced by processing hematologic parametric data obtained from other systems, or other instruments, or even on the basis of calculated hematologic parametric data, whether calculated by machine or humanly so.

The QBC II system is described in literature available from the manufacturer; refer to BI 14 to BI 17. Aspects of the QBC II are described in professional journal literature; see BI 18, BI 19. Briefly stated here, the QBC II system includes preparation of an examinee's blood specimen or assay in a special blood-tube, known as buffy coat analysis tube (see BI14 to BI17; BI19), placing this tube in a centrifuge and subjecting it to centrifugal action as described in BI14, BI16, BI17, see also BI18; and then emplacing the tube in an instrument termed QBC II (the QBC II proper) and positioning it on the instrument in six (for venous blood) or seven (for capillary blood) discrete positions, as described in BI6 to BI9. The QBC II instrument proper produces visual numeric indication, not just of the four parameters H P G L, but three additional numeric parameters indications, for a total of seven. The three additional parameters will be discussed below.

The QBC II instrument visual indication is by means of a display, on the instrument panel, produced by light-emissive-diodes. Additionally, and optionally, a computer-printer, such as Epson, Model LX 86 may be plugged into the QBC II instrument and the seven-parameter numerics will also be printed. For the purposes of this description, it may be assumed that as a minimum, the H P G L numerics have been provided to the user of the System of the present invention, by personal reading of the QBC II instrument, or by his or her reading the instrument-printer's printout currently as the printout is being made, or reading it at a later time, or by communication to the operator currently or later by voice or in writing, or electronically. The System will recompute and print out the three additional parametric numerics, whether the operator initially knew their values or not.

The QBC II instrument displays, and its printer prints the numerics for the altogether seven parameters. The system of the invention re-prints all seven, although it receives as inputs only the four mentioned H P L G. Such a re-print is shown in Appendix 1. As seen there, H is expressed as percentage, whereas P L G are each expressed in $\times 10^9$/L, or multiply by $10^9$/L. A fifth parameter, W B C or Total W B C (White Blood Cell Count) is also expressed in $10^9$/L. The sixth and seventh parameters indicate Percent Granulocytes and Percent Lymphs+Monos, respectively. Thus, the latter two are related to the parameters G and L previously discussed.

It has been stated above, that the present invention may be practiced with a personal computer, and it will be described in that manner, by way of example.

FIGS. 1, 2

Referring to FIG. 1, shown there is a computer (CPTR) or data processor 10 which may be assumed to be a personal computer, for example IBM PC Model AT. The computer 10 is equipped with the usual peripheral devices, namely a cathode ray tube (CRT) monitor or screen 12, and printer (PTR) 14, which for example may be Epson printer, Model LX 86. The computer 10 is further equipped with the usual keyboard (KBD) 16, and a receptacle 18, in which a memory storage device, such as a magnetic "floppy disk" 20 is received. It may be assumed that the computer 10 has been pre-conditioned, to PL/M-86 language; that language is explained in BI 20. The floppy disk 20 stores the knowledge base of the expert system; "knowledge base" is used in the sense of BI 2 and BI 4. As applied to the expert system here under consideration, knowledge base will be detailed below. Suffice it to state here, the knowledge base embraces the mass of hematological/diagnostic knowledge of the kind presented in BI1, from which mass of knowledge there is to be extracted the particular knowledge applicable to the four parametric numerics H P G L obtained from the hematological instrument, for example the QBC II, or else obtained by calculation. The disk 20 further stores the "inference engine"—usage of this term is also as in BI 2—broadly stated at this time, inference engine implies the processing, by the Apparatus, on the basis of the four parametric numerics, as applied to the knowledge base, to produce the applicable diagnostic printouts of the kind shown in Appendix 1.

The disk 20 in place shall be assumed to be part of the memory storage of the computer 10. The keyboard 16 is used by the Operator to enter the four basic parametric numerics for H P G L. Basically, the operator will enter via the keyboard 16 merely the four numerics; the printer 14 will subsequently print, side-by-side to the same numerics respectively, descriptive phrases of the kind shown in the examples of Appendix 1. Following the entry of the four numerics, the operator will follow this by depressing either the letter-key "S" or the letter-key "L". "S" implies the "short mode" and further implies a command to the Apparatus to execute in the short mode. "L" analogously implies selection of the "long mode" and a command to the Apparatus to execute in the long mode. Appendix 1 includes examples of short-mode, and long-mode presentation; more on these examples under the heading "The Expert System" (FIG. 3; Appendix 1); also, more on the manner of discrimination between "L" and "S" execution of the system, below. Depression of "S" or "L" being also an "execute" command, the system proceeds to print out documents of the kind shown in Appendix 1.

Referring to FIG. 2, the computer 10 is shown in block form with the usual internal equipment associated with this type of personal computer. Its memory storage facility, in addition to the disk (DK) 20, includes a random access memory (RAM) 22 and a read-only-memory (ROM) 24. It will be appreciated that the memories 22 and 24 could each be considered in plural stage or group form rather than necessarily being a sole unit. For the disk 20 there is provided the usual disk drive (DDR) 26. The computer 10 further includes the usual central processing unit (CPU) 28 which performs the processing required by the present invention, that is the processing required by the "inference engine" to be presently discussed with reference to FIGS. 3 and 4. Such processing also includes some operations which are arithmetic-type computations in the truest sense. Finally, the computer 10 includes input-output units (I/Os), or interfaces 30.

THE EXPERT SYSTEM (FIG. 3; Appendix 1)

Referring to FIG. 3, the expert system is assigned reference numeral 100. It is composed of two major sub-blocks, namely the knowledge base 102 and the inference engine 104. The general definitions given for knowledge base and inference engine should be continued; elaborations thereon will be given below. As shown in FIG. 3, the general flow is four parametric numerics in-going into the inference engine 104, and also knowledge base information in-going to the inference engine 104. Outgoing of the inference engine 104 are printouts of the kind shown in Appendix 1. Additional consideration of the latter printouts, at this point, is useful in preparation for the further description of FIG. 3, and also of FIG. 4.

For Appendix 1, dual identification of pages is used. The pages are numbered consecutively by 1.1, 1.2, 1.3 etc. Secondly, the pages are identified by hematocrit (H) value, and "short mode" (S) or "long mode" (L). The meaning of these modes will be explained below. Typically for other pages, the identificationd of Appendix pages 1.1, 1.2 are H 40/S and H 40/L respectively.

Appendix page 1.1 (H 40/S) is applicable to a patient exhibiting all hematologic values within normal limits. This page indicates three kinds of so-called reminders which form part of the knowledge base 102. Side-by-side to the reprinted four basic numerics for H P G L are "descriptive" reminders, also termed "qualitative reminders" and sometimes termed "descriptors" or "qualitative phrases". ANEMIA (see BI 13, page 17) generated similar descriptors, in a somewhat differing context. Indicated next on Appendix page 1.1 is a second kind of reminder, there given as "General Hematologic Clinical Reminders", or simply hematologic reminders. Next follows a third kind of reminder, given on Appendix page 1.1 as "Diagnostic Considerations," or simply diagnostic reminder.

Digressing briefly from Appendix 1, the fourth kind of reminder, termed "subcase reminder" will under certain circumstances appear as subordinate to the hematologic reminder or the diagnostic reminder. This happens when the hematologic or diagnostic reminder embraces a rather broad range, whereas the subordinate subcase reminder applies to a narrow range which lies within the broader range, and that narrow range is applicable to the patient.

Reverting again to Appendix 1, page 1.2 (H 40/L) is a long-mode printout; its four H P G L values are respectively the same as those of H 40/S and apply to the same patient. Similarly, Appendix 1 pages 1.3 and 1.4 (H 53/S and H 53/L) apply to one and the same patient. From here on a single printout (short or long made) per quartet of HDGL numerics, will be given in some instances. On pages 1.2 (H 40/L) and 1.4 (H 53/L) the reminders appear as "complete messages;" each complete message consists of "header" and "body" of message. On pages 1.1 (H 40/S) and 1.3 (H 53/S) merely the headers are shown. Note on pages 1.3 and 1.4 (H 53/S and /L) the presence of multiple, and in this instance two hematologic reminders. This implies multiple (two) "hits" or "successes" in the sense of the specification introduction, as will be more fully elaborated in the description of FIG. 4.

Another exemplary printout, is presented in Appendix page 1.5 (H 49.9/S). The diagnostic reminder thereat is unusual in that: (1) at the location where one would expect a "header", there appears a statement which more nearly resembles a "body," but should be construed as a header. In the corresponding long-mode version (not shown), exactly the same diagnostic reminder would appear. The System declines to give a diagnostic reminder (in the truest sense) on the basis of the HPGL values, and suggests more testing. More on this specific reminder at "Miscellaneous Matters" (conclusion of description).

In regard to the discrimination, by the Apparatus, in presenting headers only for short mode, but headers and bodies in the long mode, this is accomplished as follows. The hematologic and diagnostic reminder messages are stored in memory, in an arrangement such that the header information, stored in bytes (1 byte=8 bits), is concluded with an artificial byte, which in turn is followed by "body" bytes which conclude with an end-of-message byte. The artificial byte is a pseudo-end-of-message byte. It is interpreted as the end-of-message in short mode, so that the message retrieval ends at the end of the header. In long mode, the System ignores the artificial byte, and continues on its retrieval through the body of the message, to the true end of the message.

Other printouts, which involve so-called Technical Alerts (probably or definitely invalid input data) appear in Appendix 9, and will be discussed under the headings "Technical Alerts" and "Modifications".

The Knowledge Base—Continued (FIG. 3)

Refer again to FIG. 3 for further consideration of the knowledge base 102. Part of the knowledge base is the definition or demarcation of the boundaries of the CIIs (clinically important intervals). This is shown in Appendix 2—CII Summary. That Summary is organized, in the first instance, by the four parameters H P G L, and then individually for each, the respective CIIs assigned to it. Thus, H is assigned twelve CIIs or ranges, P eight, G ten and L eight, as had already been indicated in the specification introduction. The tabulation for H is typical also for the other parameters; for each CII the applicable hematocrit range is shown, plus the descriptor or descriptive reminder, previously mentioned.

The knowledge base block 102, following "CII Boundaries" lists the Reminder Types—these have been described above—also Priority Information, Applicable and Null Domains—these will be discussed; and finally reminder Texts—these have been discussed with reference to Appendix 1; further aspects of the reminder texts will be discussed under the next heading.

The Knowledge Base—Continued (Appendices 3, 4)

Appendix 3 presents a compact form of the knowledge base. It has been stated previously, in the specification introduction that the number of messages is about 70, and this number embraces both the diagnostic messages and the hematological messages. More accurately, and speaking as of 1986/1987, the number stands at 69; the system approach is to assign the number sequence 0 to 68, rather than 1 to 69; Appendix 3 is organized in this manner. Incidentally, concerning the previous discussion of multiple (rather than single) messages, these multiple messages are intended to apply within one and the same rubric, either hematologic or diagnostic. Thus, in the example given on Appendix page 1.1 or 1.2 (H · 40/S or /L) there is just one single hematologic message and one single diagnostic message. However, these two reminders, in the sense of Appendices 3 and 4, stem from separate ones in the series 0 to 68, and more specifically from No. 13 for the hematologic reminder, and No. 53 for the diagnostic reminder. Correspondingly, these two messages, (No. 13, No. 53) will be stored at separate locations in memory. The diagnostic reminder of Appendix page 1.5 (H 49.9/S) is not contained in the series 0 to 68; see "Miscellaneous Matters."

Refer to Appendix 3 and consider the initially presented No. 0, and the listings appearing underneath it. The line-item TYPE H indicates that the reminder is hemotologic. The next line-item DOM H will be passed for the time being. The next four line-items define the "Applicable Domain" for No. 0. Thus, for each of the four parameters H P G L a respective range of CIIs is given, which range is applicable for No. 0.

Consider the following Table 1, which re-lists the four parametric numerics given for the example in Appendix 1 page 1.1; next it tabulates the respective applicable CIIs as obtained from Appendix 2; and then it presents the respective CIIs listed for Nos. 0, 13, 53 in Appendix 3.

TABLE 1

| Example 1 App. 1, p. 1.1 | | CII (App. 2) | CII/No. 0 (App. 3) | CII/No. 13 (App. 3) | CII/No. 53 (App. 3) |
|---|---|---|---|---|---|
| H | 40 | 6 | 6–8 | 6–8 | 6–7 |
| P | 254 | 5 | 1–8 | 5–5 | 5–5 |
| G | 5.0 | 5 | 1–10 | 4–5 | 4–5 |
| L | 3.0 | 4 | 1–8 | 4–4 | 4–4 |

Seemingly No. 0 (Appendix 3) would qualify, but yet it does not, or better stated the qualification is overruled by what appears in the concluding five lines of No. 0 in Appendix 3. The first of these five lines reads null, meaning that the null domain for No. 0 is defined by the respective ranges of CIIs given for the four parameters, in the last four lines for No. 0, namely H: 6-8; P: 5-5 (meaning simply 5); G: 4-5; L: 4-4 (simply 4).

Both the applicable domain and the null domain require the existence of a logical AND condition for the CIIs under consideration. The null domain is a more restricted range of CIIs which fall respectively within the CIIs of the applicable domains. How the "overruling by the null domain is accomplished" will be explained with reference to FIG. 4.

Further inspection of Table 1 reveals that in Appendix 3, No. 13 for type H reminder and No. 53 for type D reminder satisfy the example given in Table 1, and accordingly the respective messages for No. 13 and No. 53 will be printed out.

In Appendix 3, Subcases arise for Nos. 34 to 38, and others. For No. 34, its line item S2 means (typically): Subcase for No. 2. More on this subsequently.

We now revert to the consideration of the line-item DOM H which appears for No. 0 in Appendix 3; this implies "H is dominant". This is part of the priority information indicated in block 102 in FIG. 3. The priority contemplated here, comes into full force and play when multiple hematologic messages or multiple diagnostic messages qualify for printout, that is when "multiple hits" or "multiple successes" exist. The priority scheme of the System orders these multiple messages according to factors such as clinical urgency and incidence.

While for No. 0 H is dominant, for No. 47 no parameters at all are dominant, whereas for Nos. 43, 32, 14 there appear, respectively, two, three, all four parameters. Referring also Appendix 2, the tabulation of CIIs is also part of the knowledge base or data base, and so is an allocation of degree of abnormality for each CII. Weights—also part of the knowledge base—which rank from 0 to 4 are assigned to each CII in accordance with the degree of abnormality; thus, for H (see Appendix 3, first page) the CIIs 5 to 8 would each be accorded the weight 0, whereas the CIIs 1 and 12 would be accorded the weight 4. Similar considerations apply to the other three parameters P G L.

A "dominance multiplier" is allocated to each of the four parameters; the multiplier is a number very close to 1; more specifically:

H—1.100; P—1.010; G—1.001; L—1.000.

In the case of multiple "hits", during execution of the instructions, to be described with reference to FIG. 4, for each applicable dominant parameter, its respective weight is multiplied by its respective dominance multiplier, and the resulting multiplication products are summed; the resulting sum might be termed, "priority-score-number." This number is computed for each hematologic message which qualifies for printout, and printout occurs in the order of highest priority-scorenumber. Analogous processing occurs for the qualifying diagnostic reminders. The scheme of weight assignments and dominance multipliers is to provide tie-breaking priority allocations for situations where otherwise ties among several messages would exist. The relative values of dominance multipliers assure that other things being equal among the plural messages, the messages triggered by abnormal hematocrit will be printed first, etc. If despite all these measure taken, a tie nevertheless comes about, the "tied" messages will be printed out in the order first retrieved, first printed out.

Appendix 4—Reminder Summary, on page 4.1 reflects for Nos. 0, 1, 2, 3 information which repeats that given in Appendix 3 and adds to it the respective message headers, and the parametric numeric ranges applicable to the respective CIIs. Appendix page 4.2 presents the respective complete message text (header and body) for Nos. 0 to 3 in order. Refer again to Table 1, and the discussion underneath it which points to the fact that the hematologic message applicable to the printout shown in Appendix 1, page 1.2 applies to No. 13 of Appendix 3. That complete hematologic message of No. 13, as well as the complete hematologic message No. 0, both apply to normal hematocrit, but there are some differences between these two complete messages. This is because Nos. 13 and 0 arise under mutually exclusive conditions. Still other reminder texts are presented in other examples in Appendix 1. Reminder Texts is the last item listed in the block 102, the Knowledge Base, of FIG. 3, and indeed completes the description of FIG. 3.

FIG. 4

Reference is now made to FIG. 4 which is an operational flow chart for the System. Recall, in connection with the description of FIGS. 1 and 2 that the operation is initiated by entering the four parametric numerics via the keyboard 16 and selection of the long mode by entering the letter L, or the short mode by entering the letter S. In consequence, the System begins to execute the instructions stored in the memory facilities, by determining the CIIs of the four parameters or arguments H P L G which are applicable to the four input numerics, as represented by the block 202 in FIG. 4. This step might also be termed a preselection of the applicable CIIs; referring to Appendix 2, that one of the twelve available CIIs for H is selected which is applicable to the H value of the input numeric, together with its descriptor (see Appendix 2), and similarly for the remaining three parameters or arguments P G L.

In the next step, (block 204) the indication "output" implies "prepare for printout." The just-entered four numerics, together with the descriptive phrases (Appendix 2)—just fetched out of memory—are prepared for printout.

The next block 206 calls for retrieval of "Reminder Sets for Input CIIs." The retrieved reminder sets are four in number, namely one for the applicable CII for each respective parameter H P G L. The set is a selection of all those numbers from the sequence No. 0 to No. 68 (Appendix 3) which applied to the selected CII in question.

Noting from Table 1 the applicable CII, namely H: 6; P: 5; G: 5; L: 4, let Appendix 3 be scanned for the reminder set Nos. applicable to H CII=6. The result would be that the following Nos. satisfy H CII=6:

TABLE 2

<u>0</u>; 3 to 11; <u>13</u>; 21; 23 to 27; 31; 33; 35 to 39; 41; 42; <u>53</u> to 56; 65; 67.

Note the presence of reminder set Nos. 0, 13, 53 as would be expected from previous consideration of Table 1. In effect, we have just now scanned the reminder set to single out the reminder Nos. applicable to H CII=6. The reader need not trouble to make a similar scanning for the remaining parameters P L G, because this is all shown compactly in Appendix 5.

In Appendix 5 are shown the declarations for the twelve possible CIIs for H; then those for the eight CIIs for P; then those for the ten for G; and then the eight for L. The numbering given for the CIIs begins, in each instance, with one (1). On the other hand, the numbering of the reminder set Nos. and their relative columnar positions, begins with zero (0). The CII presentation of Appendix 5, and indeed the remaining contents of Appendix 5 are stored in the memory facility of the System as part of the knowledge base.

In Appendix 5 each CII is arranged as a bit string which in turn is arranged as nine bytes; the numbering of these bytes, for the purposes of the present discussion, begins with one (1). The bytes are arranged in binary format; since there are eight bits per byte, a total of 9×8=72 columnar positions are available; numbering, for purposes of this sentence and the next sentence begins with one (1). The seventy-two positions adequately accommodate the sixty-nine reminder sets defined in Appendix 3 in the sequence 0 to 68; recall that this sequence (and hence the columnar positions) do not embrace the diagnostic reminder message of Appendix page 1.5, (H 49.9/S); see "Miscellaneous Matters". For the next ensuing discussion, it will be convenient to continue in terms of byte numbering from one to nine and of the CII numbering from one to twelve (for H, and typical for the others). The numbering of the available columnar positions will be deemed to run from 0 to 71, with a progression from left to right, and the numbering of the bit positions within a byte, extending from 0 to 7, with the progression from left to right. Following the bit position seven, each byte terminates with suffix-letter B which stands for binary (rather than, for example, D—decimal). However, even "binary" should be construed with some caution; consider the first or left-most byte in CII No. 1 for P. This byte reads 11111111; this should not be construed to mean a numeric value of 255 (decimal expression). Rather, the suffix-letter B implies that each one of the bit-positions of this byte contains a binary 1, or is "set" or is "up" or "on".

Only those bit-positions which are set, possibly qualify for retrieval of the related reminder set (Appendix 3); in any position where binary 0 ("reset" or "down" or "off") appears, retrieval is inherently disqualified.

Reverting to Table 2, above, and also scanning left-to-right the CII 6 for H in Appendix 5, the reader will arrive at bit-positions which correspond numerically to the reminder set Nos. appearing in Table 2. In operation, and referring again to the block 206 of FIG. 4, the System will retrieve from memory, for H, its CII 6, and as per the example of Table 1, for P its CII 5, for G its CII 5, and for L its CII 4; the formats for these CIIs are as shown in Appendix 5.

The next step is shown in block 208 of FIG. 4. The System computes the intersections of the reminder sets; this is done by executing the logical AND function, bit-position by bit-position in the successive columns (Appendix 5) for the four applicable parametrics CIIs. To survive for possible further qualification for printout it is necessary that a binary 1 appear in each one of the four applicable CII-representation (Appendix 5) in a given column. Referring to Appendix 5, and also Table 1, Nos. 0, 13, 53 will survive. The System (block 210, FIG. 4) next eliminates or excludes reminders for which the applicable input CIIs are in null-domains, in this instance No. 0 (see Appendix 3). As has been stated previously, exclusion of a reminder by null-domain inhibition also requires presence of logical AND condition in the four applicable CIIs. In this instance reminder No. 0 is eliminated, but Nos. 13 and 53 will remain.

Processing now continues on a basis of the characteristics applicable to the remaining reminders Nos., in this instance 13 and 53, as these characteristics are represented in Appendix 3. In the next step, block 212 of FIG. 4, the remaining reminders are classified as to type, namely hematological, diagnostic, or subcase. Supplementing the previous statements regarding subcases, it is remarked here that subcase reminders may arise in conjunction with either hematological reminders or diagnostic reminders. The subcase reminder will be printed immediately after some particular hematological or diagnostic reminder of which it is a subcase. Reverting to the consideration of Appendix 3, No. 34 as a subcase of No. 2, whenever message No. 34 qualifies for printout inherently message No. 2 likewise qualifies, and possibly still other messages might qualify in some of the parametric CII ranges for No. 34. However, the processor in effect senses the designator S2 (see Appendix 3) for No. 34, and will print out No. 34 immediately following No. 2, independently of other priority considerations. More on this point at "Miscellaneous Matters".

The next two steps are represented by the blocks 214 and 216 of FIG. 4. The step or block 214 calls for computing parameter weights; the step or block 216 calls for computing priority ranking of hematological reminders. These two steps have been described in connection with a description of FIG. 3, and the knowledge base. Supplementing that previous discussion the actual dominant factor data is stored in a memory location which is specified by a data declaration arranged in an array of bytes in hex format (BI20, Appendix E) where each byte contains the dominant factor information for the respective reminder message. The dominant factor information is encoded in the four bits of the upper nibble (1 nibble=one half byte) of each byte as follows: H: bit 7; P: bit 6; G: bit 5; L: bit 4; numbering descends from 7 to 0 (total: eight).

If the bit is set, that parameter is dominant for the respective reminder message. As has been pointed out previously the reminder message may have more than one dominant parameter. Attention has also been directed to reminders without dominant parameters, such as No. 47 (Appendix 3). This implies that the reminder No. 47 be printed last. The System, in proceeding from step 214 to step 216 and ultimately to step 220 (Compute Priority Ranking of Diagnostic Reminders), inherently makes its own priority selection as between all remaining hematological reminders (plus their subcases) on the one hand—these are preferred—and all remaining diagnostic reminders (plus their subcases) on the other hand. This is on the basis of the reminder—type indication as presented for the individual reminders in Appendix 3.

In the next step or block 218 (FIG. 4) the remaining hematological reminders and any subcases are fully retrieved, prepared for printing ("output"), in the format as presented in Appendix 4, and in the priority order decided upon in the step 216.

The steps 220 and 222 are analogous to the steps 216 and 218, but apply to the diagnostic reminders and their subcases. As to the processing of the diagnostic reminder of Appendix page 1.5, see "Miscellaneous Matters." As the final step 224 the System prints out all "outputs" in the order 204, 218, 222, in either short mode or long mode, and with priority ranking as described for the steps 216, 220. In regard to the "output" steps 204, 218, 222, and the printout step 224 the System locates by way of a "lookup table" the memory addresses which correspond to the reminder texts to printed out. Although there is a numerical correspondence of message numbers (total 69; numbering begins with one) and memory addresses, yet the memory stores much other information besides the messages, and accordingly has a much greater number of addresses.

Appendix 6 presents the program, in PL/M-86 Compiler language, which the expert System executes in proceeding through the steps shown in FIG. 4. For explanation of this Compiler language, the reader is referred to BI 20.

CREATION OF THE EXPERT SYSTEM

The immediately preceding section concluded with a reference to Appendix 6, which reflects the program to be executed by the System, expressed in PL/M-86 Compiler language (BI20). In this section there will be described the preparation or creation of the Expert System, more or less from the beginning until one arrives at Appendix 6. What now follows is one possible manner of creation of the System and alternative approaches are probably possible.

As a starter, the knowledge base in human language, is prepared on the basis of BI 1, the knowledge engineer's own knowledge, and reference to other authorities. This work entails the creation of the reminder messages, the establishment of the clinically important intervals (CIIs), the allocation of the messages to the CIIs, the specification of the dominant factors, and more generally the items and matters which in the preceding description have been allocated to the knowledge base. When the Expert System is operational, the items required to be printed out, i.e., the messages will come back in human language (Appendix 1). However, at the time of creation or preparation of the Expert System, the reminder messages as well as the other items constituting the knowledge base need to go through code or language translation, and this is also the case for the creation of the program to be stored in the System's memory facility.

In preparation for the translation, the various items that comprise the knowledge base are entered into computer files on disk using a text editor. Then a separate computer program which is written in the C Compiler language (see BI 21) is used to perform the first step of the translation. The most important extracts of this C Compiler program are shown in Appendices 7 and 8. This translation program reads the computer files that represent the human-language knowledge base, and uses them to produce a representation of the knowledge base in the PL/M-86 compiler language (BI 20, Appendix 5). Not all of the PL/M-86 representation of the knowledge base is obtained by translation in this manner, however; some parts are entered directly into computer files, using a text editor. Thus, we have two sources of PL/M-86 representation. Finally, the PL/M86 language compiler is used to translate the PL/M-86 source files, obtained from the two sources, into computer-executable code which may be stored, for example, on a floppy disk. The System may then be readied for operation.

MISCELLANEOUS MATTERS

Regarding the diagnostic reminder message of Appendix page 1.5 (H 49.9/S) it will be recalled that the message attempts no diagnostic indication in the truest sense. Furthermore, it has been remarked that this message is not contained in the sequence 0 to 68 of Appendix 3, nor in the seventy-two columnar positions of Appendix 5. Additionally, the message is not retrieved in the step 206 (FIG. 4), nor is it prepared for printout by the steps 220, 222 of FIG. 4. Instead, applicability of the message is ascertained "in default" of any other diagnostic message at step 212, and thereupon at step 222, the Appendix page 1.5 (H 49.9/S) message is retrieved from a special location in memory. Considering that this message occurs rather frequently, the just discussed handling is simpler than handling in the same manner as the other messages.

Regarding the discussion of subcases, it is additionally remarked here, that as to the subcases tabulated in Appendix 3 (Nos. 34 to 38, 40, 41), speaking as of late 1986/early 1987 each of these subcases is subordinate to a hematologic reminder message (in the series 0 to 68), none to a diagnostic reminder message. Hence the mentioning, in the block 218, 222 (FIG. 4) of diagnostic subcases implies that the System is presently equipped to handle a matter which is "reserved for possible future use"; another such "future reservation" concerns the assignment of dominance factors to subcases.

Refer again to Appendix 3, and in particular to No. 35, which has designators Type S10, DOM P, and then to its superordinate No. 10 which has designators Type M, DOM M. Should No. 35 be applicable, No. 10 will inherently be applicable; the No. 35 message will be integrated into, and follow immediately the No. 10 message, regardless of other priority considerations. DOM H will apply to the integrated No. 10, not DOM P of No. 35 considered separately. Seemingly the DOM P of No. 35 has no meaning, and yet it does. The System allows for the possible future contingencies of allocating multiple subcases to one and the some superordinate message, with priority allocation among such subcases, on the basis of their dominance factors and weighting, much in the some manner as for non-subcase messages.

TECHNICAL ALERTS

Technical alerts are messages which indicate invalid combinations of HPGL numerics, some indicated to be unconditionally invalid, others merely possibly or likely or conditionally so. It should be noted that ANEMIA (BI 13, page 19) monitored input data for invalidity. An important feature of the System is that the technical alert suggests the likely error by the human operator which induced the invalid instrument readings.

Examples of technical alerts are shown in the Appendix 9 print outs. Appendix pages 9.1, 9.2, 9.3 present one example of a technical alert, among the diagnostic messages. By analogy to the Appendix 1 pages, page 9.1 may be identified as H 15/S, page 9.2 as H 15/L, but since the long mode print out extends onto a second or continuation page 9.3, that page 9.3 might be considered H 15/L2. The technical alert in the H 15 printouts is conditional; it suggests several possible operator errors such as blood leakage. However, the HPGL numerics are compatible with pancytopenia, and suggests repetition of the test, and then acceptance as valid, the repetition of the measurements.

Appendix page 9.4 (H 63/S) presents a more nearly unconditional technical alert; there are no alternative valid diagnostic reminders.

Appendix page 9.5 (H 28.2/S) does present alternative valid diagnostic reminders, and hence should be regarded as presenting a conditional technical alert. Appendix page 9.6 (H 28.2/S) which is an alternative short-mode version to page 9.5, will be discussed in the next section.

MODIFICATIONS

The described system admits of various modifications. For example, the number of stored messages (Appendix 3) could be readily increased.

Some potential user-physicians have indicated a preference for printing out diagnostic messages before hemotologic messages. This is readily achieved by interchanging the priority of the designator, D over H, in the sense of the flow in FIG. 4. Hand-in-hand with this modification is a proposed modification to single out technical alerts (designator T) as a separate grouping of messages, apart from diagnostic and hematologic messages, and give them highest priority. This too is readily implemented following the previously given teachings. Appendix page 9.6 (H 28.2/S) indicates the T first, D second, H third arrangement.

CONCLUSION

From the foregoing it is seen that by the present invention there has been provided a practically useful hemotology diagnostic system. Among its advantages are:

Human language output presentation. This is in contrast to a prior scheme which employed cryptic computer-type coding which led to commission of errors by non-computer trained physicians.

Operability on the basis of consistently the same number, and same small number of that, and the same kind of input parameters (HPGL) with their numerics all obtained from a single data source (QBC II). This has led to simple equipment which may be installed and readily used in many physicians' offices. This is in contrast to the prior systems, of which only one of its kind was made available at a university research center, there to serve the world at large.

A noninteractive expert system is used. This has the decided advantage, that advice is given to the physician in "one shot", rather than the mutual repeated interrogations required by prior art approaches. The user of the system need not be a computer expert.

The System does not forget important information, does not become tired, distracted or rushed, and so provides a consistently high quality interpretation of numerical results.

BIBLIOGRAPHY

BI 1. Wintrobe, M. M.; Clinical Hematology, 8th Edition.

BI 2. Mishkoff, Henry C.; Understanding Artificial Intelligence; Copyright 1985, Howard W. Sams & Co., Indianapolis, Ind., U.S.A.; Chapter 3: Expert Systems (pp. 53-77); Glossary (pp. 251-254); see also Bibliography (pp. 247-249).

BI 3. Winston, Patrick Henry; Artificial Intelligence; Second Printing, 1979 (Copyright 1977), Addison-Wesley Publishing Company, Reading, Mass., U.S.A.; Chapter 7: Representing Knowledge in Frames (pp. 179-204).

BI 4. U.S. Pat. No. 4,591,983, Bennett et al., published May 27, 1986.

BI 5. U.S. Pat. No. 4,648,044, Hardy et al., published Mar. 3, 1987.

BI 6. U.S. Pat. No. 4,658,370, Erman et al., published Apr. 14, 1987—Medical—Diagnostic Expert Systems literature listed under References Cited/Other Publications.

BI 7. Waterman, Donald A.; A Guide to Expert Systems; Addison-Wesley Publishing Company, Reading, Mass., U.S.A., Copyright 1986; pp. 273-289: Catalog of Expert Systems/Medicine; see also Bibliography pp. 319-329.

BI 8. Artificial Intelligence Reporter, January 1986 issue: A Reference Guide to Medical Expert Systems, pp. 3, 12; Books on Medical AI, pp. 9, 10.

BI 9. to BI 12. Co-authors are Engle, Ralph L., and Flehinger, Betty J.

BI 9. HEME: A Computer Aid to Diagnosis of Hematologic Disease; Bulletin-New York Academy of Medicine, Vol. 52, No. 15, June 1976, pp. 584-600.

BI 10. HEME: A Self-Improving Computer Program for Diagnosis-Oriented Analysis of Hematological Diseases; IBM Journal of Research and Development, Vol. 19, pp. 557-564, November 1975.

BI 11. HEME 2: A Long History of Computer-Aided Hematologic Diagnosis; IEEE Convention Record 1982, pp. 763-767.

BI 12. Computer Aids to Diagnosis; Research Report No. RC 6872 (Environmental Sciences), published by IBM Research Division, Yorktown Heights, N.Y., U.S.A., December 1977; pp. 1-12.

BI 13. S. Quaglini et al.; ANEMIA: An Expert Consultation System; Computers and Biomedical Research, Vol. 19, pp. 13-27, 1986; published by Academic Press, Inc.

BI 14. Operator's Manual for the QBC II Centrifugal Hematology System, published by Becton Dickinson (B-D) (Revision B, dated October, 1984).

BI 15. Brochure 4200-000-003/AWBC-572 published by B-D, March, 1984.

BI 16. Brochure AWBC-1079, published by B-D, May, 1986.

BI 17. Brochure DM-QBC-TS-4Q, published by B-D, 1986.

BI 18. Sallitt, Robert L. et al., Evaluation of Leukocyte Centrifugal Counts; Blood Cells (Periodical), published by Springer-Verlag, November 1985 issue, pp. 281-294.

BI 19. Wardlaw, Stephen C. et al., Quantitative Buffy Coat Analysis, Journal of the American Medical Association, Vol. 249, No. 5, Feb. 4, 1983, pp. 617-620.

BI 20. PL/M-86 User's Guide for DOS Systems, Intel Corporation, Santa Clara, Calif. 95051, U.S.A. Copyright 1985; Chapters 1-3 (PL-M-86 language); Appendix E-ASCII (American Standard Codes for Information Interchange) Character Codes.

BI 21. Microsoft C Compiler for the MS-DOS Operating System, User's Guide; Microsoft Corporation, Copyright 1984, 1985, 1986; Main Text—C Language; Appendix A—ASCII Character Codes.

| INDEX TO APPENDICES | | |
|---|---|---|
| APPENDIX No. | SUBJECT MATTER | SPECIFICATION |
| 1 | Typical Diagnositic Printouts | |
| 2 | CII Summary | |
| 3 | Knowledge Base | |
| 4 | Reminder Summary | |
| 5 | Generation of Bit Stings PL/M-86 Compiler | |
| 6 | Expert System Program PL/M-86 Compiler | |
| 7 | Generation of Reminder Messgaes Microsoft C Compiler Version | |
| 8 | Generation of Bitstrings Microsoft C Compiler Version | |
| 9 | Technical Alerts | |

```
Physician's Diagnostic Reminders
QBC Centrifugal Hematology System

Written By: Robert A. Levine, M.D.
Edited By: Maxwell M. Wintrobe, M.D.

Hematocrit (%)           =  48.0  normal value for adult males:   40-54%
                                  normal value for adult females: 37-47%

Platelets (x10^9/L)      =  254   within normal range

Total WBC (x10^9/L)      =  8.0

Percent Granulocytes     =  63
Granulocytes (x10^9/L)   =  5.0   within normal range Percent Lymphs+Monos     =  37
Lymphs+Monos (x10^9/L)   =  3.0   within normal range
```

GENERAL HEMATOLOGIC CLINICAL REMINDERS:

THE REPORTED HEMATOLOGIC VALUES ARE WITHIN NORMAL LIMITS FOR ADULTS.

SPECIFIC DIAGNOSTIC CONSIDERATIONS INCLUDE:

NORMAL.

```
Hematocrit (%)            =  40.0   normal value for adult males:   40-54%,
                                    normal value for adult females: 37-47%

Platelets (x10^9/L)       =  254    within normal range

Total WBC (x10^9/L)       =  8.0

Percent Granulocytes      =  63
Granulocytes (x10^9/L)    =  5.0    within normal range Percent Lymphs+Monos      =  37
Lymphs+Monos (x10^9/L)    =  3.0    within normal range
```

GENERAL HEMATOLOGIC CLINICAL REMINDERS:

THE REPORTED HEMATOLOGIC VALUES ARE WITHIN NORMAL LIMITS FOR ADULTS.

The reported hematologic parameters are within normal limits. This does not rule out the presence of disease. If the detection of eosinophilia is clinically important, an examination of the peripheral smear should be performed. The results, especially the hematocrit, should be compared to baseline values for the patient in order to discover changes from earlier findings. The normal hematocrit values for adults, 40-54% for males and 37-47% for females, are determined for patients at sea level; at higher altitudes add 2% for each 4000 ft. (1200 meters). In infants and children the normal hematocrit values are higher than in adults for the first two months of life, lower afterwards and gradually rise until puberty. Wintrobe, M.M.; Clinical Hematology, Ed. 8, pp. 1885, 1888, 1893, 356, 372.

SPECIFIC DIAGNOSTIC CONSIDERATIONS INCLUDE:

NORMAL.

The reported hematologic values are within the adult normal range.

```
Hematocrit (%)            =  53.0   normal value for adult males:   40-54%,
                                    normal value for adult females: 37-47%

Platelets (x10^9/L)       =  247    within normal range

Total WBC (x10^9/L)       =  28.5

Percent Granulocytes      =  15
Granulocytes (x10^9/L)    =  4.3    within normal range Percent Lymphs+Monos      =  85
Lymphs+Monos (x10^9/L)    =  24.2   extremely elevated
```

GENERAL HEMATOLOGIC CLINICAL REMINDERS:

LYMPHOCYTOSIS/MONOCYTOSIS.

NORMAL HEMATOCRIT.

MILD OR BORDERLINE POLYCYTHEMIA (ERYTHROCYTOSIS).

SPECIFIC DIAGNOSTIC CONSIDERATIONS INCLUDE:

LEUKEMOID REACTION (LYMPHOID TYPE).

| | | |
|---|---|---|
| Hematocrit (%) | = 53.0 | normal value for adult males: 40-54%, normal value for adult females: 37-47% |
| Platelets ($\times 10^9$/L) | = 247 | within normal range |
| Total WBC ($\times 10^9$/L) | = 28.5 | |
| Percent Granulocytes | = 15 | |
| Granulocytes ($\times 10^9$/L) | = 4.3 | within normal range |
| Percent Lymphs+Monos | = 85 | |
| Lymphs+Monos ($\times 10^9$/L) | = 24.2 | extremely elevated |

GENERAL HEMATOLOGIC CLINICAL REMINDERS:

LYMPHOCYTOSIS/MONOCYTOSIS.

Increases in lymphocytes/monocytes may be due to (a) infectious mononucleosis, (b) certain acute infections (e.g., pertussis, infectious hepatitis, and cytomegalovirus infection) and certain chronic infections (e.g., tuberculosis, brucellosis, secondary and congenital syphilis), (c) certain protozoal infections, (d) some lymphomas and in certain acute leukemias (blast cells may enlarge the lymph/mono layer) and (e) chronic lymphocytic leukemia. Additional tests include an examination of the peripheral smear and those suggested by review of history and physical examination. Wintrobe, M.M.; Clinical Hematology, Ed. 8, pp. 1285-1287.

MILD OR BORDERLINE POLYCYTHEMIA (ERYTHROCYTOSIS).

The upper limit of normal hematocrit values is 54 for adult males and 47 for adult females. Patients who smoke or who live above sea level may have elevated hematocrits. The normal hematocrit values for adults, 40-54% for males and 37-47% for females, are determined for patients at sea level; at higher altitudes add 2% for each 4000 ft. (1200 meters). In infants and children the normal hematocrit values are higher than in adults for the first two months of life, lower afterwards and gradually rise until puberty. Wintrobe, M.M.; Clinical Hematology, Ed. 8, p. 1885, Table A-1, A-3; 1891, Table A-15.

DIAGNOSTIC CONSIDERATIONS AND WARNINGS:

LEUKEMOID REACTION (LYMPHOID TYPE).

A high lymphocyte count consisting mostly of mature lymphocytes, thus simulating chronic lymphocytic leukemia (CLL), has been seen in infants and young children with pertussis. A CLL picture has been associated with other diseases including dermatitis herpetiformis, exfoliative dermatitis, chicken pox, cancer of the stomach, metastatic melanoma, breast cancer, and miliary tuberculosis. Wintrobe, M.M.; Clinical Hematology, Ed. 8, p. 1316.

```
Hematocrit (%)          = 49.9    normal value for adult males:   40-54%,
                                  normal value for adult females: 37-47%

Platelets (x10^9/L)     = 525     moderately elevated

Total WBC (x10^9/L)     = 31.5

Percent Granulocytes    = 65
Granulocytes (x10^9/L)  = 20.5    markedly elevated Percent Lymphs+Monos    = 35
Lymphs+Monos (x10^9/L)  = 11.0    moderately elevated
```

GENERAL HEMATOLOGIC CLINICAL REMINDERS:

MARKED GRANULOCYTOSIS.
  THROMBOCYTOSIS.
  LYMPHOCYTOSIS/MONOCYTOSIS.
  NORMAL HEMATOCRIT.

SPECIFIC DIAGNOSTIC CONSIDERATIONS INCLUDE:

The pattern of hematologic values obtained is not specific enough to suggest a given diagnosis or syndrome. Further steps to be taken will depend on the patient's history, physical examination, and examination of the blood smear.

CBC CII SUMMARY

Fri Feb 20 15:39:45 1987

HEMATOCRIT (%, ROUNDED TO 2 DECIMAL PLACE(S))
----------

```
CII #   HEMATOCRIT RANGE           DESCRIPTOR
        (after rounding)

1.      0.0  -  9.9               extremely decreased 2.     10.0  - 15.9               extremely decreased 3.     16.0  - 25.9               markedly decreased 4.     26.0  - 33.9               markedly decreased 5.     34.0  - 36.9     normal value for adult males:   40-54%,
                         normal value for adult females: 37-47%

6.     37.0  - 41.9     normal value for adult males:   40-54%,
                         normal value for adult females: 37-47%

7.     42.0  - 50.9     normal value for adult males:   40-54%,
                         normal value for adult females: 37-47%

8.     51.0  - 54.9     normal value for adult males:   40-54%,
                         normal value for adult females: 37-47%

9.     55.0  - 59.9               moderately elevated
```

| 10. | 60.0 - 65.9 | markedly elevated |
| 11. | 66.0 - 75.9 | extremely elevated |
| 12. | 76.0 - max | extremely elevated |

PLATELETS (x10^9/L, ROUNDED TO 0 DECIMAL PLACE(S))

| CII # | PLATELET RANGE (after rounding) | DESCRIPTOR |
|---|---|---|
| 1. | 0.0 - 19.0 | extremely decreased |
| 2. | 20.0 - 39.0 | extremely decreased |
| 3. | 40.0 - 79.0 | markedly decreased |
| 4. | 80.0 - 139.0 | moderately decreased |
| 5. | 140.0 - 440.0 | within normal range |
| 6. | 441.0 - 700.0 | moderately elevated |
| 7. | 701.0 - 998.0 | markedly elevated |
| 8. | 999.0 - max | extremely elevated |

GRANULOCYTES (x10^9/L, ROUNDED TO 1 DECIMAL PLACE(S))

| CII # | GRANULOCYTE RANGE (after rounding) | DESCRIPTOR |
|---|---|---|
| 1. | 0.0 - 0.9 | extremely decreased |
| 2. | 1.0 - 1.5 | moderately decreased |
| 3. | 1.6 - 1.7 | moderately decreased |
| 4. | 1.8 - 3.0 | within normal range |
| 5. | 3.1 - 7.2 | within normal range |
| 6. | 7.3 - 9.0 | moderately elevated |
| 7. | 9.1 - 10.0 | moderately elevated |
| 8. | 10.1 - 15.0 | moderately elevated |
| 9. | 15.1 - 35.0 | markedly elevated |
| 10. | 35.1 - max | markedly elevated |

LYMPHS & MONOS (x10^9/L, ROUNDED TO 1 DECIMAL PLACE(S))

| CII # | LYMPHS & MONOS RANGE (after rounding) | DESCRIPTOR |
|---|---|---|
| 1. | 0.0 - 0.5 | extremely decreased |
| 2. | 0.6 - 1.0 | markedly decreased |
| 3. | 1.1 - 1.6 | slightly below normal range |

| | | | |
|---|---|---|---|
| 4. | 1.7 - 4.9 | within normal range |
| 5. | 5.0 - 6.0 | slightly elevated |
| 6. | 6.1 - 12.0 | moderately elevated |
| 7. | 12.1 - 20.0 | markedly elevated |
| 8. | 20.1 - max | extremely elevated |

```
type kb.txt >prn

# 0             # 7              # 13             # 21            # 26
TYPE    H      TYPE    H        TYPE    H        TYPE    D       TYPE    D
DOM     H      DOM     L        DOM              DOM     P       DOM     L
H 6-8          H 1-12           H 6-8            H 5-8           H 6-8
P 1-8          P 1-8            P 5-5            P 1-3           P 4-5
G 1-18         G 1-18           G 4-5            G 4-6           G 2-5
L 1-8          L 5-8            L 4-4            L 4-5           L 5-7
NULL                                                             NULL
H 6-8          # 8              # 14             # 22            H 6-8
P 5-5          TYPE    H        TYPE    D        TYPE    D       P 4-5
G 4-5          DOM     G        DOM     H P G L  DOM     L       G 2-2
L 4-4          H 3-3            H 3-5            H 2-4           L 5-5
               P 1-8            P 5-7            P 4-8
# 1            G 1-4            G 3-9            G 3-9           # 27
TYPE    H      L 3-5            L 3-6            L 3-4           TYPE    D
DOM     H      NULL                              NULL            DOM     L
H 1-5          H 1-12           # 15             H 3-4           H 6-8
P 1-8          P 1-8            TYPE    D        P 5-6           P 4-5
G 1-18         G 3-3            DOM              G 4-7           G 2-5
L 1-8          L 4-4            H 2-3            L 3-4           L 5-7
                                P 5-5                            NULL
# 2            H 1-12           G 5-7            # 23            H 6-8
TYPE    H      P 1-8            L 3-4            TYPE    D       P 4-5
DOM     H      G 4-4                             DOM     P       G 2-2
H 9-12         L 3-4            # 16             H 5-8           L 5-5
P 1-8          NULL             TYPE    D        P 7-8
G 1-18         H 1-12           DOM              G 8-9           # 28
L 1-8          P 1-8            H 3-3            L 4-5           TYPE    D
               G 3-3            P 5-5                            DOM     H
# 3            L 3-3            G 4-5            # 24            H 3-5
TYPE    H                       L 3-4            TYPE    D       P 1-4
DOM     G      # 9                               DOM     G       G 1-3
H 1-12         TYPE    H        # 17             H 5-8           L 3-5
P 1-8          DOM     L        TYPE    D         5-6            NULL
G 1-1          H 1-12           DOM              G 8-18          H 5-5
L 1-8          P 1-8            H 4-4            L 7-8           P 4-4
               G 1-18           P 5-5                            G 1-3
# 4            L 1-3            G 4-5            # 25            L 3-5
TYPE    H                       L 3-4            TYPE    D
DOM     G      # 10                              DOM     L       # 29
H 1-12         TYPE    H        # 18             H 6-8           TYPE    D
P 1-8          DOM     P        TYPE    D        P 5-5           DOM     L
G 2-3          H 5-12           DOM     H        G 4-5           H 2-4
L 1-8          P 1-4            H 2-4            L 8-8           P 1-4
               G 4-18           P 4-5                            G 1-3
               L 1-8            G 2-4                            L 6-8
# 5                             L 3-4                            NULL
TYPE    H      # 11                                              H 4-4
DOM     G      TYPE    H        # 19                             P 4-4
H 1-12         DOM     P        TYPE    D                        G 3-3
P 1-8          H 1-12           DOM     P L G                    L 6-6
G 6-8          P 6-8            H 4-5
L 1-8          G 1-18           P 4-6
               L 1-8            G 3-7
```

```
# 6                          L 3-5
TYPE    H     # 12
DOM     6     TYPE    D     # 28
H 1-12        DOM     H 6 P TYPE    D
P 1-8         H 1-4         DOM     H
6 9-10        P 1-4         H 2-4
L 1-8         6 1-3         P 2-4
              L 2-5         6 7-9
                            L 3-5

# 30           # 36          # 43          # 48          # 55          # 62
TYPE    D      TYPE   S 10   TYPE    D     TYPE    H     TYPE    D     TYPE    H
DOM     H      DOM    P      DOM     H 6   DOM     H     DOM     6     DOM     H
H 8-11         H 5-12        H 7-8         H 6-7         H 5-8         H 8-8
P 5-8          P 2-2         P 5-5         P 6-8         P 5-6         P 1-8
6 4-10         6 4-10        6 6-7         6 1-3         6 2-3         6 1-10
L 4-4          L 1-8         L 4-4         L 5-8         L 4-5         L 1-8
NULL
H 8-8          # 37          # 44          # 49          # 56          # 63
P 5-5          TYPE   S 12   TYPE    D     TYPE    H     TYPE    D     TYPE    D
6 4-7          DOM    P      DOM     H     DOM     H     DOM     L     DOM     L
L 4-4          H 5-12        H 2-5         H 6-7         H 4-7         H 4-5
               P 3-3         P 4-5         P 5-8         P 4-6         P 5-5
# 31           6 4-10        6 2-4         6 5-10        6 4-6         6 7-8
TYPE    D      L 1-8         L 3-4         L 1-3         L 1-1         L 1-3
DOM     L                    NULL
H 4-7                        H 5-5         # 50          # 57          # 64
P 3-5          # 38          P 5-5         TYPE    H     TYPE    D     TYPE    H
6 4-5          TYPE   S 10   6 3-4         DOM     H     DOM     P     DOM     P
L 8-8          DOM    P      L 3-4         H 6-7         H 2-5         H 1-4
               H 5-12        NULL          P 6-8         P 3-4         P 1-4
# 32           P 4-4         H 4-4         6 5-10        6 2-3         6 4-10
TYPE    D      6 4-10        P 5-5         L 5-8         L 3-4         L 1-8
DOM     P 6 L  L 1-8         6 4-4
H 1-5                        L 3-4         # 51          # 58          # 65
P 1-3          # 39                        TYPE    D     TYPE    D     TYPE    H
6 1-2          TYPE    D     # 45          DOM     H     DOM     P     DOM     P
L 1-3          DOM     L     TYPE    D     H 1-3         H 2-5         H 5-12
NULL           H 5-7         DOM     L     P 7-8         P 3-4         P 1-4
H 5-5          P 5-6         H 4-7         6 3-8         6 7-9         6 1-3
P 3-3          6 7-9         P 4-5         L 4-5         L 3-4         L 1-8
6 2-2          L 2-3         6 4-5
L 3-3                        L 8-8         # 52          # 59          # 66
               # 40                        TYPE    D     TYPE    D     TYPE    H
# 33           TYPE   S 1    # 46          DOM     H     DOM     H     DOM     P
TYPE    D      DOM    H      TYPE    D     H 9-12        H 1-5         H 1-4
DOM     6      H 1-3         DOM           P 1-3         P 6-8         P 1-4
H 3-6          P 1-8         H 2-4         6 3-6         6 6-9         6 1-3
P 4-8          6 1-10        P 1-4         L 3-4         L 2-4         L 1-8
6 10-10        L 1-8         6 1-3
L 4-4                        L 6-8         # 53          # 60          # 67
               # 41          NULL          TYPE    D     TYPE    D     TYPE    D
               TYPE   S 11   H 4-4         DOM           DOM     L H   DOM     G
# 34           DOM    P      P 4-4         H 6-7         H 4-5         H 3-6
TYPE    S 2    H 1-12        6 3-3         P 5-5         P 4-5         P 5-9
DOM     H      P 7-8         L 6-6         6 4-5         6 3-5         6 10-10
H 10-12        6 1-10                      L 4-4         L 5-7         L 5-8
P 1-8          L 1-8         # 47
6 1-10                       TYPE    D     # 54          # 61          # 68
L 1-8          # 42          DOM     L     TYPE    H     TYPE    D     TYPE    H
               TYPE    D     H 5-5         DOM     L     DOM     L H   DOM     H 6
# 35           DOM     L     P 5-5         H 5-8         H 4-5         H 1-4
TYPE    S 10   H 6-7         6 4-5         P 5-5         P 4-5         P 5-6
DOM     P      P 4-5                                                   6 1-3
```

```
H 5-12      G 6-8           L 3-4      G 3-5       G 6-8       L 2-5
P 1-1       L 5-7                      L 5-6       L 5-7
G 4-10
L 1-8                                                           (: PLA\WCRX)
```

OBC REMINDER SUMMARY

Fri Feb 20 15:39:11 1987

```
# 0
NORMAL HEMATOCRIT.
type:  Hematological
dom:   H
applicable domain:
        ciis            actual values (after rounding)
   H:   6  -   8        37.0   -   55.0   %
   P:   1  -   8         0.0   -   max    x10^9/L
   G:   1  -  10         0.0   -   max    x10^9/L
   L:   1  -   8         0.0   -   max    x10^9/L
null domain:
   H:   6  -   8        37.0   -   55.0   %
   P:   5  -   5       140.0   -  440.0   x10^9/L
   G:   4  -   5         1.8   -    7.2   x10^9/L
   L:   4  -   4         1.7   -    4.9   x10^9/L

# 1
ANEMIA.
type:  Hematological
dom:   H
applicable domain:
        ciis            actual values (after rounding)
   H:   1  -   5         0.0   -   37.0   %
   P:   1  -   8         0.0   -   max    x10^9/L
   G:   1  -  10         0.0   -   max    x10^9/L
   L:   1  -   8         0.0   -   max    x10^9/L

# 2
POLYCYTHEMIA (ERYTHROCYTOSIS).
type:  Hematological
dom:   H
applicable domain:
        ciis            actual values (after rounding)
   H:   9  -  12        55.0   -   max    %
   P:   1  -   8         0.0   -   max    x10^9/L
   G:   1  -  10         0.0   -   max    x10^9/L
   L:   1  -   8         0.0   -   max    x10^9/L

# 3
SEVERE GRANULOCYTOPENIA.
type:  Hematological
dom:   G
applicable domain:
        ciis            actual values (after rounding)
   H:   1  -  12         0.0   -   max    %
   P:   1  -   8         0.0   -   max    x10^9/L
   G:   1  -   1         0.0   -    0.9   x10^9/L
   L:   1  -   8         0.0   -   max    x10^9/L
```

NORMAL HEMATOCRIT.

The normal hematocrit values for adults, 40-54% for males and 37-47% for females, are determined for patients at sea level; at higher altitudes add 2% for each 4000 ft. (1200 meters). In infants and children the normal hematocrit values are higher than in adults for the first two months of life, lower afterwards and gradually rise until puberty. Wintrobe, M.M.; Clinical Hematology, Ed. 8, p. 1885, Table A-1, A-3; 1891, Table A-15.

ANEMIA.

Hematocrit values that are below normal signal anemia. Anemia can be due to (a) acute or chronic blood loss, (b) decreased red cell production, caused by infection or inflammation, hypoplasia, neoplasm, or nutritional deficiency, (c) increased red cell destruction\hemolytic anemia. The nature and cause of the anemia should be determined. Suggested additional tests include an examination of the peripheral smear and determination of red blood cell indices as well as a reticulocyte count. Additional tests may include testing the stool for the presence of occult blood and parasites, as well as determination of the total and fractionated serum bilirubin and urinary evidences of hemoglobin breakdown. Wintrobe, M. M.; Clinical Hematology, Ed. 8, pp. 529-558 and Table 20-1, p. 541.

POLYCYTHEMIA (ERYTHROCYTOSIS).

Hematocrit values that are above normal (polycythemia) may be caused by a reduction in plasmal volume ("relative" polycythemia) or by "absolute" polycythemia due to increased red cell mass caused by chronic hypoxemia, or to polycythemia vera or other disorders. Suggested additional tests include an examination of the peripheral smear and other tests appropriate to the results of the history and physical examination (e.g. enquiring about causes of relative polycythemia such as dehydration, exposure to toxic agents). Wintrobe, M. M.; Clinical Hematology, Ed. 8, pp. 991-1010.

SEVERE GRANULOCYTOPENIA.

Granulocyte counts of $0.5 \times 10^{9}/L$ or less present a great risk of infection. Their cause must be sought. Prophylactic antibiotic therapy is generally required. Severely decreased granulocyte counts may be drug induced (aminopyrine, phenothiazines, sulfonamides, antithyroids, and gold are common examples) or chemotherapy induced. Aplastic anemia also is a cause. Milder degrees of granulocytopenia may be seen in certain infections (typhoid, paratyphoid, measles, infectious hepatitis, infectious mononucleosis, malaria, brucellosis and most rickettsial diseases).. Impaired production of granulocytes may be due to megaloblastic anemia, especially pernicious anemia. Cachexia or debilitated states, systemic lupus erythematosus, splenomegaly and anaphylaxis also are possible causes. Additional tests include those suggested by specific enquiries as to the clinical manifestations of these disorders, as well as those tests indicated by the results of the physical examination. Wintrobe, M.M.; Clinical Hematology, Ed. 8, pp.1304-1312.

PL/M-86 COMPILER     QBC     EXPERT SYSTEM, SECOND DATA MODULE                          03/10/87 10:42:55

DOS 3.20 (038-N) PL/M-86 V2.7 COMPILATION OF MODULE EXPDATA2
OBJECT MODULE PLACED IN \PLM\OBJ\EXPDATA2.OBJ
COMPILER INVOKED BY: C:\PLM\PLM86.EXE \PLM\EXPDATA2.SRF SET(PCSFLAG=255) OBJECT(\PLM\OBJ\EXPDATA2.OBJ)
                     PRINT(\PLM\LLST\EXPDATA2.LST)

$TITLE(' QBC    EXPERT SYSTEM, SECOND DATA MODULE ')

$IF PCSFLAG = FALSE
        $INCLUDE(PLMCON.INC)

```
          $ELSE
          $COMPACT
          $ENDIF

EXPDATA2: DO;
          $INCLUDE(GLOBLITS.INC)
=         $SAVE
=         $NOLIST
          $INCLUDE(EXPLITS.INC)
=         $SAVE
=         $NOLIST

/***********************************************************
           *     QBC EXPERT SYSTEM DATA MODULE 2
           *
           *  THIS MODULE CONTAINS THE DATA DECLARATIONS FOR THE BITSTRINGS
           *  REPRESENTING APPLICABLE REMINDERS, THE STRUCTURES FOR THE NULL
           *  DOMAINS, AND THE ARRAYS OF DOMINANT FACTORS AND REMINDER TYPES.
           *
           *  THIS FILE WAS GENERATED BY THE QBC UPDATE PROGRAM.
           *
           *  Joan Curry
           *  Becton Dickinson Research Center
           *
           *  Fri Feb 20 15:39:42 1987
           *
           ***********************************************************/

$EJECT
```

```
64   1    DCL H_CII (NUM_H_CIIS) STRUCTURE (BITS (NUM_REM_BYTES) BYTE) PUBLIC DATA
          (01811111B,11011100B,00000000B,00000000B,10000000B,11000000B,00010000B,00010000B,10001000B,
           01011111B,11011001B,00001010B,00000100B,10000000B,11001010B,00010000B,01100000B,10001000B,
           01011111B,11011011B,10001010B,00001100B,11000000B,11001010B,00010000B,01100000B,10011000B,
           01011111B,11011000B,01011010B,00001101B,11000000B,01001110B,00010000B,11111101B,10011000B,
           01011111B,11100001B,00010101B,10001001B,11011111B,01001101B,00000011B,11111101B,01010000B,
           10011111B,11101000B,00001011B,11100001B,01011111B,01100100B,00001111B,10000000B,01010000B,
           10011111B,11101000B,00001011B,11100001B,00011111B,01110100B,00001111B,10000000B,01000000B,
           10011111B,11101000B,00001011B,11100001B,00011111B,01100100B,00001111B,10000011B,00000000B,
           00111111B,11100000B,00000000B,00000010B,00111111B,01000000B,00010000B,00000000B,01000000B,
           00111111B,11100000B,00000000B,00000010B,10111111B,01000000B,00010000B,10000000B,01000000B,
           00111111B,11100000B,00000000B,00000010B,00111111B,01000000B,00010000B,10000000B,01000000B,
           00111111B,11100000B,00000000B,00000010B,00111111B,01000000B,00010000B,10000000B,01000000B);

65   1    DCL P_CII (NUM_P_CIIS) STRUCTURE (BITS (NUM_REM_BYTES) BYTE) PUBLIC DATA
          (11111111B,11101000B,00000100B,00001100B,10100000B,10000010B,00001000B,00000010B,11000000B,
           11111111B,11101000B,00001100B,00001100B,10101000B,10000010B,00001000B,00000010B,11000000B,
           11111111B,11101000B,00001100B,00001101B,10101100B,10000010B,00001000B,01100010B,11000000B,
           11111111B,11101000B,00011000B,00111101B,01100010B,10101110B,00000000B,11101110B,11000000B,
           11111111B,11000111B,10100000B,11110011B,01100001B,10111101B,00000111B,10001111B,00010005B,
           11111111B,11010000B,00000100B,10000010B,01100001B,10000000B,00000001B,10010010B,00010000B,
           11111111B,11010000B,00000111B,00000010B,01100000B,11000000B,00010000B,00010010B,00010005B,
           11111111B,11010000B,00000111B,00000010B,01100000B,11000000B,00010000B,00010010B,00010005B);

66   1    DCL G_CII (NUM_G_CIIS) STRUCTURE (BITS (NUM_REM_BYTES) BYTE) PUBLIC DATA
          (11110001B,11011000B,00000000B,00001100B,10100000B,11000010B,00000000B,00000010B,01001000B,
           11101001B,11011000B,00000000B,10111100B,10100000B,11001010B,00000010B,01001010B,01001000B,
           11101001B,11011010B,00010010B,10111100B,00100000B,11010100B,00010011B,01010010B,01001000B,
           11100001B,11101100B,10101100B,01100011B,00111100B,11001100B,00011100B,00010000B,10000000B,
           11100001B,01110111B,10101100B,01100011B,00111111B,11001010B,00010000B,00010000B,10000000B,
           11100001B,01100011B,00010000B,00000010B,00111111B,11100000B,00010000B,00010000B,10000000B,
           11100001B,01100011B,00010100B,00000010B,00111111B,11100000B,00010000B,00010111B,10000000B,
           11100001B,01100100B,00010100B,00000010B,00111111B,11100000B,00010000B,00010111B,10000000B,
           11100011B,01100100B,00010100B,00000010B,00111111B,11100000B,00010000B,00010111B,10000000B,
           11100011B,01100100B,00000000B,10000010B,01111110B,11000000B,00000010B,00000010B,10010000B);
```

```
67  1    DCL L_CII (NUM_L_CIIS) STRUCTURE (BITS (NUM_REM_BYTES) BYTE) PUBLIC DATA
             (11111110B,01110000B,00000000B,00000000B,10111110B,11000000B,00000000B,10000011B,11000000B,
              11111110B,01110000B,00000000B,00000000B,10111111B,11000000B,00000000B,00010011B,11001000B,
              11111110B,11111011B,11011010B,00001000B,10111111B,11001001B,00001000B,01100011B,11001000B,
              11111110B,10111111B,11011111B,10001010B,01111111B,11011001B,00011101B,01110010B,11001000B,
              11111111B,10111010B,00011121B,00111000B,00111110B,11100000B,00100011B,00001110B,11011000B,
              11111111B,00110010B,00000000B,00110100B,00111110B,11100010B,00000010B,00001110B,11010000B,
              11111111B,00110000B,00000000B,00110100B,00111110B,11100010B,00000000B,00001110B,11010000B,
              11111111B,00110000B,00000000B,01000010B,00111110B,11000110B,00000000B,00000100B,11010000B);

68  1    DCL NULLS (TOTAL_NUM_NULLS) STRUCTURE
             .REM_NUM BYTE,
             H_LO BYTE, H_HI BYTE,
             P_LO BYTE, P_HI BYTE,
             G_LO BYTE, G_HI BYTE,
             L_LO BYTE, L_HI BYTE) PUBLIC DATA
                ( 0,   5,   7,   4,   4,   3,   4,   3,   3,
                  6,   0,  11,   0,   7,   2,   2,   3,   3,
                  8,   0,  11,   0,   7,   3,   3,   2,   3,
                  8,   0,  11,   0,   7,   2,   2,   2,   2,
                 22,   2,   3,   4,   5,   3,   6,   2,   3,
                 26,   5,   7,   3,   4,   1,   1,   4,   4,
                 27,   5,   7,   3,   4,   1,   1,   4,   4,
                 28,   4,   4,   3,   3,   0,   2,   2,   4,
                 29,   3,   3,   3,   3,   2,   2,   5,   5,
                 30,   7,   7,   4,   4,   3,   6,   3,   3,
                 32,   4,   4,   2,   2,   1,   1,   2,   2,
                 44,   4,   4,   4,   4,   2,   3,   2,   3,
                 44,   3,   3,   4,   4,   3,   3,   2,   3,
                 46,   3,   3,   3,   3,   2,   2,   5,   5);

89  1    DCL REM_TYPE (TOTAL_NUM_REMS) BYTE PUBLIC DATA
             ( HEMAT_TYPE, HEMAT_TYPE, HEMAT_TYPE, HEMAT_TYPE, HEMAT_TYPE, HEMAT_TYPE, HEMAT_TYPE, HEMAT_TYPE, HEMAT_T
                -YPE, HEMAT_TYPE,
               HEMAT_TYPE, HEMAT_TYPE, DIAG_TYPE , HEMAT_TYPE, DIAG_TYPE , DIAG_TYPE , DIAG_TYPE , DIAG_TYPE , HEMAT_T
                -YPE, DIAG_TYPE ,
               DIAG_TYPE , DIAG_TYPE , DIAG_TYPE , DIAG_TYPE , DIAG_TYPE , DIAG_TYPE , DIAG_TYPE , DIAG_TYPE , DIAG_TY
                -PE , DIAG_TYPE ,
               DIAG_TYPE , DIAG_TYPE , DIAG_TYPE , DIAG_TYPE , 2         , 10        , 10        , 10        , 10
                , DIAG_TYPE ,
               1         , 11        , DIAG_TYPE , DIAG_TYPE , DIAG_TYPE , DIAG_TYPE , DIAG_TYPE , DIAG_TYPE , HEMAT_T
                -YPE, HEMAT_TYPE,
               HEMAT_TYPE, DIAG_TYPE , DIAG_TYPE , DIAG_TYPE , HEMAT_TYPE, DIAG_TYPE , DIAG_TYPE , DIAG_TYPE , DIAG_TY
                -PE , DIAG_TYPE ,
               DIAG_TYPE , DIAG_TYPE , HEMAT_TYPE, DIAG_TYPE , HEMAT_TYPE, HEMAT_TYPE, HEMAT_TYPE, DIAG_TYPE , HEMAT_T
                -YPE);

90  1    DCL DOMINANT_FACTORS (TOTAL_NUM_REMS) BYTE PUBLIC DATA
             (080H, 080H, 080H, 020H, 020H, 020H, 020H, 010H, 020H, 010H,
              040H, 040H, 0E0H, 00H, 0F0H, 00H, 00H, 00H, 00H, 070H,
              080H, 040H, 010H, 040H, 020H, 010H, 010H, 010H, 080H, 010H,
              060H, 010H, 070H, 020H, 080H, 040H, 040H, 040H, 040H, 010H,
              080H, 040H, 010H, 0A0H, 080H, 010H, 00H, 00H, 00H, 00H,
              00H, 080H, 080H, 00H, 010H, 020H, 010H, 040H, 040H, 080H,
              090H, 090H, 080H, 010H, 040H, 040H, 00H, 020H, 0A0H);

91  1    END$MODULE EXPDATA2;

MODULE INFORMATION:

CODE AREA SIZE     = 0000H      0D
    CONSTANT AREA SIZE = 025EH    606D
    VARIABLE AREA SIZE = 0000H      0D
    MAXIMUM STACK SIZE = 0000H      0D
    257 LINES READ
```

0 PROGRAM WARNINGS
0 PROGRAM ERRORS

DICTIONARY SUMMARY:

347KB MEMORY AVAILABLE
   8KB MEMORY USED   (2%)
   0KB DISK SPACE USED

END OF PL/M-86 COMPILATION

DOS 3.20 (038-N) PL/M-86 V2.7 COMPILATION OF MODULE EXPERTSYSTEM
OBJECT MODULE PLACED IN \PLM\OBJ\EXPERT.OBJ
COMPILER INVOKED BY:  C:\PLM\PLM86.EXE \PLM\EXPERT.SRF SET(PC$FLAG=255) OBJECT(\PLM\OBJ\EXPERT.OBJ)
                PRINT(\PLM\LLST\EXPERT.LST)

$TITLE (' QBC    EXPERT SYSTEM ')

$IF PC$FLAG = FALSE
              $INCLUDE(PLMCON.INC)
              $ELSE
              $COMPACT
              $ENDIF

1          EXPERT$SYSTEM: DO;
              $INCLUDE(EXPHEADER.INC)
  =           /********************************************************/
  =           /*                                                      */
  =           /*         BECTON DICKINSON RESEARCH CENTER             */
  =           /*         21 DAVIS DRIVE                               */
  =           /*         RESEARCH TRIANGLE PARK, N.C.                 */
  =           /*         (919) 549-8641                               */
  =           /*                                                      */
  =           /*         APPLIED PHYSICS DEPARTMENT                   */
  =           /*                                                      */
  =           /*         EXPERT SYSTEM SOFTWARE FOR THE               */
  =           /*         QBC   PHYSICIANS MODULAR OFFICE SYSTEM       */
  =           /*                                                      */
  =           /********************************************************/

=           $EJECT
              $INCLUDE(GLOBLITS.INC)
  =           $SAVE
  =           $NOLIST
              $INCLUDE(EXPLITS.INC)
  =           $SAVE
  =           $NOLIST
              $INCLUDE(USFSP2.INC)
  =           $SAVE
  =           $NOLIST

/***********************************************************
               *         QBC    EXPERT SYSTEM MODULE
               * THIS MODULE IS PART OF A SUBSYSTEM TO THE QBC-III CONTROL
               * PROGRAM. THE FUNCTION OF THIS MODULE IS TO INTERPRET THE
               * HEMATOLOGIC RESULTS OF A QBC TUBE ASSAY. UPON SUCESSFUL
               * INTERPRETATION THIS MODULE WILL PROVIDE THE NECESSARY INFO
               * VIA AN EXPERT SYSTEM INTERFACE BLOCK, TO THE MAIN MODULE.
               * IN ADDITION, THIS MODULE WILL RETURN A NUMBER TO INFORM
               * THE MAIN MODULE HOW MANY ENTRIES IT HAS PUT IN THE EXPERT
               * INTERFACE BLOCK, EACH ENTRY BEING A STRING TO BE PRINTED.
               *
               * LAST MODIFIED 11/86 TO ADD NULL DOMAINS AND FIX UP
               *    DOCUMENTATION -- CURRY.
               ***********************************************************/

```
/**************** EXTERNAL DATA ***********************
 *
 *  REM_ADDRESS is from the module EIPMSG.
 *  The following are from EIPDATA2:
 *      H_CII, P_CII, G_CII, L_CII
 *      NULLS
 *      REM_TYPE
 *      DOMINANT_FACTORS
 *  All the rest of these are from EIPDATA.
 */
```

149  1     DCL REM_ADDRESS (TOTAL_NUM_REMS) PTR EXT DATA;
                   /* references to all the reminder messages */

150  1     DCL H_CII (NUM_H_CIIS) STRUCTURE  (BITS (NUM_REM_BYTES) BYTE) EXT DATA;
151  1     DCL P_CII (NUM_P_CIIS) STRUCTURE  (BITS (NUM_REM_BYTES) BYTE) EXT DATA;
152  1     DCL G_CII (NUM_G_CIIS) STRUCTURE  (BITS (NUM_REM_BYTES) BYTE) EXT DATA;
153  1     DCL L_CII (NUM_L_CIIS) STRUCTURE  (BITS (NUM_REM_BYTES) BYTE) EXT DATA;
                   /* bit strings to indicate which reminders are applicable
                                  in which ranges for each QBC parameter */

154  1     DCL NULLS (TOTAL_NUM_NULLS) STRUCTURE
                  (REM_NUM BYTE,
                   H_LO BYTE, H_HI BYTE,
                   P_LO BYTE, P_HI BYTE,
                   G_LO BYTE, G_HI BYTE,
                   L_LO BYTE, L_HI BYTE) EXT DATA;
                   /* lower and upper bounds, in ciis, of a 'null' or exclusion domain */

155  1     DCL REM_TYPE (TOTAL_NUM_REMS) BYTE EXT DATA;
                   /* map from reminder numbers to reminder types: hematological,
                              diagnostic, or subcase */

156  1     DCL DOMINANT_FACTORS (TOTAL_NUM_REMS) BYTE EXT DATA;
                   /* map from reminder nums to symbolic bytes indicating dominant
                              factors, which are subsets of the 4 QBC params */

157  1     DCL H_CII_BOUNDS  (NUM_H_CIIS)  REAL EXT DATA;
158  1     DCL P_CII_BOUNDS  (NUM_P_CIIS)  REAL EXT DATA;
159  1     DCL G_CII_BOUNDS  (NUM_G_CIIS)  REAL EXT DATA;
160  1     DCL L_CII_BOUNDS  (NUM_L_CIIS)  REAL EXT DATA;
                   /* lower bounds of clinically important intervals */

161  1     DCL H_CII_MAP (NUM_H_CIIS) BYTE EXT DATA;
162  1     DCL P_CII_MAP (NUM_P_CIIS) BYTE EXT DATA;
163  1     DCL G_CII_MAP (NUM_G_CIIS) BYTE EXT DATA;
164  1     DCL L_CII_MAP (NUM_L_CIIS) BYTE EXT DATA;
                   /* maps from ciis to cii descriptor numbers */

165  1     DCL DESCRIPTOR_WT (NUM_DESCRIPTORS) BYTE EXT DATA;
                   /* map from descriptor numbers to weights, for ordering
                              the reminders used in compute_param_wts */

166  1     DCL H_DESCRIPTOR_ADDR (NUM_DESCRIPTORS) PTR EXT DATA;
167  1     DCL P_DESCRIPTOR_ADDR (NUM_DESCRIPTORS) PTR EXT DATA;
168  1     DCL G_DESCRIPTOR_ADDR (NUM_DESCRIPTORS) PTR EXT DATA;
169  1     DCL L_DESCRIPTOR_ADDR (NUM_DESCRIPTORS) PTR EXT DATA;
                   /* maps from descriptor numbers to addresses of descriptor strings */

```
170  1    DCL TIE_BREAKER_WT STRUCTURE
              (H REAL, P REAL, G REAL, L REAL) EXT DATA;
              /* numbers we'll multiply the param wts by to break ties in wt */

171  1    DCL H_LABEL    (*) BYTE EXT DATA;
172  1    DCL P_LABEL    (*) BYTE EXT DATA;
173  1    DCL WBC_LABEL  (*) BYTE EXT DATA;
174  1    DCL PC_E_LABEL (*) BYTE EXT DATA;
175  1    DCL VAL_E_LABEL(*) BYTE EXT DATA;
176  1    DCL PC_L_LABEL (*) BYTE EXT DATA;
177  1    DCL VAL_L_LABEL(*) BYTE EXT DATA;
              /* labels for printing assay results */

178  1    DCL HEMAT_HEADER (*) BYTE EXT DATA;
179  1    DCL DIAG_HEADER  (*) BYTE EXT DATA;
180  1    DCL NO_DIAG      (*) BYTE EXT DATA;
181  1    DCL DISCLAIMER   (*) BYTE EXT DATA;
182  1    DCL COPYRIGHT    (*) BYTE EXT DATA;
183  1    DCL TITLE1       (*) BYTE EXT DATA;
184  1    DCL TITLE2       (*) BYTE EXT DATA;
185  1    DCL TITLE3       (*) BYTE EXT DATA;
              /* other stuff to print */

/******************* EXTERNAL PROCEDURES *******************
 *
 *   Both of these are from EATOI.
 */

186  1    EFLOAT$TO$ASCII:
              PROC (VAR$PTR, S$PTR, BUF$LEN, D$COUNT) EXT;
187  2        DCL VAR$PTR PTR;
188  2        DCL S$PTR PTR;
189  2        DCL BUF$LEN BYTE;
190  2        DCL D$COUNT BYTE;
191  2    END_PROC EFLOAT$TO$ASCII;

192  1    I$TO$ASCII:
              PROC(N, S$PTR) EXT;
193  2        DCL N BYTE;
194  2        DCL S$PTR PTR;
195  2    END_PROC I$TO$ASCII;

/************* OTHER EXTERNAL DECLARATIONS *****************
 *
 *   Declared in the module that calls the expert system.
 */
196  1    DCL EXP$INT$BLK (100) PTR EXT;
              /* will be set to hold strings to be printed. The expert system should
                 probably keep up with the count in order to detect overflow, in
                 the production-quality version of this. But I think the probability
                 of overflow is zero in any case. */

/******************* PRIVATE DECLARATIONS *******************
 *
 */

197  1    DCL NEXT_MSG BYTE;
              /* index into EXP$INT$BLK where next message should go */

198  1    DCL ROUNDED_QBC_RSLT STRUCTURE
              (H FLOAT$NUM, P FLOAT$NUM, G FLOAT$NUM, L FLOAT$NUM);
              /* like the input param to EXPERT$SYSTEM, but rounded off as
                 specified by Dr. Levine */
```

```
199  1    DCL H_NUM_STR      (8) BYTE,
              P_NUM_STR      (8) BYTE,
              WBC_NUM_STR    (8) BYTE,
              VAL_G_NUM_STR  (8) BYTE,
              PC_G_NUM_STR   (8) BYTE,
              VAL_L_NUM_STR  (8) BYTE,
              PC_L_NUM_STR   (8) BYTE;
              /* for displaying values of QBC parameters */
```

```
/***************************************************************
*
* Name: ROUND
*
* Function: Rounds a non-negative float$num to specified number of
*           decimal places.
*
* Parameters: P - address of the float$num.
*             D_PLACES - desired number of decimal places.
*
* Returns: Nothing. Side-effects the value referenced by P.
*
* Globals: None.
*
* Caution: Will overflow if the float$num is 'too big' or if 'too
*          many' decimal places are specified.
***************************************************************/
200  1    ROUND: PROC (P, D_PLACES);
201  2      DCL P         PTR;
202  2      DCL D_PLACES  BYTE;

203  2      DCL I         BYTE,
                TMP_WORD  WORD;
204  2      DCL FP10      FLOAT$CONST(10.0),
                FP_HALF   FLOAT$CONST(0.5);
205  2      DCL TEN       FLOAT$NUM,
                HALF      FLOAT$NUM;

206  2      STORE$CONST(@FP10, @TEN);
207  2      STORE$CONST(@FP_HALF, @HALF);

/* get digits we need to keep to left of decimal point */
208  2      DO I = 1 TO D_PLACES;
209  3        MUL(.TEN, P);
210  3      END;

/* round to nearest 1 */
211  2      ADD(.HALF, P);
212  2      TMP_WORD = EINT_COM(P);
213  2      FLOAT$INT(TMP_WORD, P);

/* put the decimal point back where it belongs */
214  2      DO I = 1 TO D_PLACES;
215  3        DIV(.TEN, P);
216  3      END;

217  2    END$PROC ROUND;

$EJECT
```

```
/***************************************************************
*
* Name: GET_INTERVAL
*
* Function: Determines in which ci1 interval an assay result falls.
*
```

```
* Parameters: P - ptr to the QBC assay rslt for some parameter,
*                non-negative, rounded off as specified by Dr. Levine.
*             BOUNDS_P - address of array of lower bounds of the cii's
*                         for this parameter.
*             NUM_INTERVALS - number of cii's for this parameter.
*
* Returns: The cii number (0-based) for this parameter. This is the
*          highest array position whose entry is <= the parameter.
*
* Globals: None.
*
**************************************************************/
```

```
218  1   GET_INTERVAL: FUNCT (P, BOUNDS_P, NUM_INTERVALS) BYTE;
219  2      DCL P            PTR;
220  2      DCL Z            BASED P FLOAT$NUM;
221  2      DCL BOUNDS_P     POINTER;
222  2      DCL BOUNDS       BASED BOUNDS_P (1) REAL; /* size num_intervals */
223  2      DCL NUM_INTERVALS BYTE;

224  2      DCL I            BYTE;
225  2      DCL TMP_FLOAT    FLOAT$NU , 226  2      I = NUM_INTERVALS - 1;
227  2      STORE$CONST(@BOUNDS(I), @TMP_FLOAT);
228  2      DO WHILE ELESS$THAN(.Z, .TMP_FLOAT);
229  3         I = I - 1;
230  3         STORE$CONST(@BOUNDS(I), @TMP_FLOAT);
231  3      END$DO$WHILE;

232  2      RETURN I;

233  2   END$FUNCT GET_INTERVAL;

$EJECT
```

```
/************************************************************
*
* Name: OUTPUT_STRING
*
* Function: Puts a string to be output into the next available position
*           of EIP$INT$BLK, and increments index for next avail. posn.
*
* Parameters: P - ptr to string to be output.
*
* Returns: Nothing.
*
* Globals: Modifies EIP$INT$BLK and NEXT_MSG.
*
**************************************************************/
```

```
234  1   OUTPUT_STRING: PROC(P);
235  2      DCL P PTR;

236  2      EIP$INT$BLK(NEXT_MSG) = P;
237  2      NEXT_MSG = NEXT_MSG + 1;

238  2   END$PROC OUTPUT_STRING;

$EJECT
```

```
/************************************************************
*
* Name: GET_PERCENT
*
* Function: Finds what percent one float$num is of another.
*
```

```
* Parameters: PART_P - ptr to a float$num, assumed non-negative.
*             WHOLE_P - ptr to a float$num, assumed non-negative.
*             PERCENT_P - if the number referenced by PART_P is X% of
*                         the number referenced by WHOLE_P, then the
*                         number referenced by PERCENT_P will be set
*                         to X. (If the "whole" is zero, the percent is
*                         set to 100.)
*
* Returns: Nothing. Modifies the float$num referenced by PERCENT_P.
*
* Globals: None.
*
********************************************************************/
```

```
239   1    GET_PERCENT: PROC(PART_P, WHOLE_P, PERCENT_P);
240   2       DCL (PART_P, WHOLE_P, PERCENT_P) PTR;

241   2       DCL FP100   FLOAT$CONST(100.0);
242   2       DCL HUNDRED FLOAT$NUM;

243   2       STORE$CONST(@FP100, @HUNDRED);

244   2       IF FP$IS$ZERO(WHOLE_P) THEN
245   2          STORE(.HUNDRED, PERCENT_P);
246   2       ELSE DO;
247   3          STORE(PART_P, PERCENT_P);
248   3          MUL(.HUNDRED, PERCENT_P);
249   3          DIV(WHOLE_P, PERCENT_P);
250   3       END;
251   2    END$PROC GET_PERCENT;

$EJECT
```

```
/********************************************************************
*
* Name: OUTPUT_SIMPLE_STUFF
*
* Function: Formats strings to be printed to display assay results and short
*           phrases or 'cii-descriptors' describing them. Note here we round
*           to same number of places as the QBC control software does, so
*           the results will be consistent with what the instrument shows.
*           Elsewhere we round as specified by Drs. Levine and Wintrobe.
*
* Parameters:
*    QBC_PTR - ptr to structure holding assay results.
*    CII_PTR - ptr to structure identifying which cii each QBC
*              parameter lies in.
*
* Returns: Nothing. Results stored in EIP$INT$BLK, and NEXT_MSG is set
*          to the offset into EIP$INT$BLK just past the last string.
*
* Globals: References a huge bunch of external data.
*          Modifies EIP$INT$BLK and NEXT_MSG.
*
* Caution: This assumes that each QBC parameter can be written with
*          <= 6 characters, including decimal point. No check is made
*          here to find out whether that's true.
*
********************************************************************/
```

```
252   1    OUTPUT_SIMPLE_STUFF: PROC(QBC_PTR, CII_PTR);
253   2       DCL QBC_PTR PTR;
254   2       DCL QBC_RSLT BASED QBC_PTR STRUCTURE (H FLOAT$NUM,
                        P FLOAT$NUM, G FLOAT$NUM, L FLOAT$NUM);
255   2       DCL CII_PTR PTR;
256   2       DCL WHICH_CII BASED CII_PTR STRUCTURE
                        (H BYTE, P BYTE, G BYTE, L BYTE);
```

```
257  2        DCL ROUNDED_QBC_RSLT STRUCTURE (H FLOAT$NUM, P FLOAT$NUM,
                              G FLOAT$NUM, L FLOAT$NUM, WBC FLOAT$NUM);
258  2        DCL (G_PERCENT, L_PERCENT) FLOAT$NUM;
259  2        DCL FP100 FLOAT$CONST(100.0);
260  2        DCL HUNDRED FLOAT$NUM;

/* round the results, as done in the QBC instrument */
261  2        STORE(.QBC_RSLT.H, .ROUNDED_QBC_RSLT.H);
262  2        STORE(.QBC_RSLT.P, .ROUNDED_QBC_RSLT.P);
263  2        STORE(.QBC_RSLT.G, .ROUNDED_QBC_RSLT.G);
264  2        STORE(.QBC_RSLT.L, .ROUNDED_QBC_RSLT.L);
265  2        CALL ROUND(.ROUNDED_QBC_RSLT.H, 1);
266  2        CALL ROUND(.ROUNDED_QBC_RSLT.P, 0);
267  2        CALL ROUND(.ROUNDED_QBC_RSLT.G, 1);
268  2        CALL ROUND(.ROUNDED_QBC_RSLT.L, 1);

/* compute wbc, using rounded grans & non-grans, as in QBC instrument */
269  2        STORE(.ROUNDED_QBC_RSLT.G, .ROUNDED_QBC_RSLT.WBC);
270  2        ADD(.ROUNDED_QBC_RSLT.L, .ROUNDED_QBC_RSLT.WBC);

/* compute percents, and round */
271  2        CALL GET_PERCENT(.ROUNDED_QBC_RSLT.G, .ROUNDED_QBC_RSLT.WBC, .G_PERCENT);
272  2        CALL ROUND(.G_PERCENT, 0);              /* 1 ????     0 ????? */
273  2        STORE$CONST(@FP100, @HUNDRED);
274  2        STORE(.G_PERCENT, .L_PERCENT);
275  2        SUB(.HUNDRED, .L_PERCENT);

/* convert to ascii */
276  2        CALL EFLOAT$TO$ASCII(.ROUNDED_QBC_RSLT.H, .H_NUM_STR, 6, 1);
277  2        CALL EFLOAT$TO$ASCII(.ROUNDED_QBC_RSLT.P, .P_NUM_STR, 6, 0);
278  2        CALL EFLOAT$TO$ASCII(.ROUNDED_QBC_RSLT.WBC, .WBC_NUM_STR, 6, 1);
279  2        CALL EFLOAT$TO$ASCII(.G_PERCENT, .PC_G_NUM_STR, 6, 0);
280  2        CALL EFLOAT$TO$ASCII(.ROUNDED_QBC_RSLT.G, .VAL_G_NUM_STR, 6, 1);
281  2        CALL EFLOAT$TO$ASCII(.L_PERCENT, .PC_L_NUM_STR, 6, 0);
282  2        CALL EFLOAT$TO$ASCII(.ROUNDED_QBC_RSLT.L, .VAL_L_NUM_STR,6,1);

/* finish formatting output */
283  2        H_NUM_STR(6) = ' ';
284  2        P_NUM_STR(6) = ' ';
285  2        WBC_NUM_STR(6) = ' ';
286  2        PC_G_NUM_STR(6) = ' ';
287  2        VAL_G_NUM_STR(6) = ' ';
288  2        PC_L_NUM_STR(6) = ' ';
289  2        VAL_L_NUM_STR(6) = ' ';
290  2        H_NUM_STR(7) = END$OF$MSG;
291  2        P_NUM_STR(7) = END$OF$MSG;
292  2        WBC_NUM_STR(7) = END$OF$MSG;
293  2        PC_G_NUM_STR(7) = END$OF$MSG;
294  2        VAL_G_NUM_STR(7) = END$OF$MSG;
295  2        PC_L_NUM_STR(7) = END$OF$MSG;
296  2        VAL_L_NUM_STR(7) = END$OF$MSG;

/* and do the output */
297  2        CALL OUTPUT_STRING(.H_LABEL);
298  2        CALL OUTPUT_STRING(.H_NUM_STR);
299  2        CALL OUTPUT_STRING(H_DESCRIPTOR_ADDR(H_CII_MAP(WHICH_CII.H)));
300  2        CALL OUTPUT_STRING(.(CR, LF, LF, END$OF$MSG));
301  2        CALL OUTPUT_STRING(.P_LABEL);
302  2        CALL OUTPUT_STRING(.P_NUM_STR);
303  2        CALL OUTPUT_STRING(P_DESCRIPTOR_ADDR(P_CII_MAP(WHICH_CII.P)));
304  2        CALL OUTPUT_STRING(.(CR, LF, LF, END$OF$MSG));
305  2        CALL OUTPUT_STRING(.WBC_LABEL);
306  2        CALL OUTPUT_STRING(.WBC_NUM_STR);
307  2        CALL OUTPUT_STRING(.(CR, LF, LF, END$OF$MSG));
308  2        CALL OUTPUT_STRING(.PC_G_LABEL);
309  2        CALL OUTPUT_STRING(.PC_G_NUM_STR);
310  2        CALL OUTPUT_STRING(.(CR, LF, END$OF$MSG));
```

```
311  2        CALL OUTPUT_STRING(.VAL_G_LABEL);
312  2        CALL OUTPUT_STRING(.VAL_G_NUM_STR);
313  2        CALL OUTPUT_STRING(G_DESCRIPTOR_ADDR(G_CII_MAP(WHICH_CII.G)));
314  2        CALL OUTPUT_STRING(.(CR, LF, LF, END$OF$MSG));
315  2        CALL OUTPUT_STRING(.PC_L_LABEL);
316  2        CALL OUTPUT_STRING(.PC_L_NUM_STR);
317  2        CALL OUTPUT_STRING(.(CR, LF, END$OF$MSG));
318  2        CALL OUTPUT_STRING(.VAL_L_LABEL);
319  2        CALL OUTPUT_STRING(.VAL_L_NUM_STR);
320  2        CALL OUTPUT_STRING(L_DESCRIPTOR_ADDR(L_CII_MAP(WHICH_CII.L)));
321  2        CALL OUTPUT_STRING(.(CR, LF, END$OF$MSG));
322  2     END$PROC OUTPUT_SIMPLE_STUFF;

$EJECT

/****************************************************************
            *
            * Name: AND_REMINDERS
            *
            * Function: Computes the logical and of the bitstrings representing
            *           sets of reminder numbers for the four QBC parameter.
            *
            * Parameters:
            *      H, P, G, NG - ptrs to the bitstrings for the four QBC params
            *      RSLP_P - and for the result.
            *
            * Returns: Nothing. Result goes into the vector referenced by RSLT_P.
            *
            * Globals: None.
            *
            ****************************************************************/
323  1     AND_REMINDERS: PROC(H, P, G, NG, RSLT_P);
324  2        DCL (H,P,G,NG,RSLT_P) POINTER;
325  2        DCL H_BITS  BASED H    (NUM_REM_BYTES) BYTE;
326  2        DCL P_BITS  BASED P    (NUM_REM_BYTES) BYTE;
327  2        DCL G_BITS  BASED G    (NUM_REM_BYTES) BYTE;
328  2        DCL L_BITS  BASED NG   (NUM_REM_BYTES) BYTE;
329  2        DCL RSLT    BASED RSLT_P (NUM_REM_BYTES) BYTE;

330  2        DCL I BYTE;

331  2        DO I = 0 TO NUM_REM_BYTES - 1;
332  3           RSLT(I) = H_BITS(I) AND P_BITS(I) AND G_BITS(I) AND L_BITS(I);
333  3        END;

334  2     END$PROC AND_REMINDERS;

$EJECT

/****************************************************************
            *
            * Name: EXTRACT_REM_NUMS
            *
            * Function: Extracts the reminder numbers implied by a bitstring
            *           representation of a reminder set, eliminates any that are
            *           in the exclusion domains for this reminder, and sorts the
            *           remaining ones by reminder type.
            *
            * Parameters:
            * => CHANGE THIS DOC!
            *      REM_BITS_P - ptr to bitstring representing set of reminder-
            *                   numbers, in which the lowest-order bit of each byte
            *                   corresponds to the lowest reminder number, and the
            *                   8th byte corresponds to the 8 lowest-numbered
            *                   reminders (ie, reminders 0-7), etc.
```

```
*       H, D, S, - ptrs to structures that will accumulate reminder
*                  numbers (and counts) for hematological, diagnostic,
*                  and subcase reminders, respectively.
*
*  Returns: Nothing. Puts results in structures passed in.
*
*  Globals: References REM_TYPE.
*           Modifies nothing.
*
*******************************************************************/
335  1    EXTRACT_REM_NUMS: PROC (REM_BITS_P, H, D, S, WHICH_CII_P);
336  2      DCL (REM_BITS_P, H, D, S, WHICH_CII_P) PTR;
337  2      DCL REM_BITS BASED REM_BITS_P (NUM_REM_BYTES) BYTE;
338  2      DCL HEMAT_REMS BASED H STRUCTURE
                    (COUNT BYTE, REM_NUM (MAX_REMS_ONE_ASSAY) BYTE);
339  2      DCL DIAG_REMS BASED D STRUCTURE
                    (COUNT BYTE, REM_NUM (MAX_REMS_ONE_ASSAY) BYTE);
340  2      DCL SUBCASE_REMS BASED S STRUCTURE
                    (COUNT BYTE, REM_NUM (MAX_REMS_ONE_ASSAY) BYTE);

341  2      DCL (I, J, REM_NUM, HOLD) BYTE;

342  2      HEMAT_REMS.COUNT = 0;
343  2      DIAG_REMS.COUNT = 0;
344  2      SUBCASE_REMS.COUNT = 0;

345  2      BYTE$LOOP: DO I = 0 TO NUM_REM_BYTES - 1;
346  3         HOLD = REM_BITS(I);
347  3         BIT$LOOP: DO J = 0 TO 7;
348  4            REM_NUM = I*8 + J;
349  4            IF ((HOLD AND 10000000B) = 10000000B) AND
                     (EXCLUDED(REM_NUM, WHICH_CII_P) = FALSE) THEN
350  4               DO;
351  5                  IF REM_TYPE(REM_NUM) = HEMAT_TYPE THEN
352  5                     DO;
353  6                        HEMAT_REMS.REM_NUM(HEMAT_REMS.COUNT) = REM_NUM;
354  6                        HEMAT_REMS.COUNT = HEMAT_REMS.COUNT + 1;
355  6                     END;
356  5                  ELSE IF REM_TYPE(REM_NUM) = DIAG_TYPE THEN
357  5                     DO;
358  6                        DIAG_REMS.REM_NUM(DIAG_REMS.COUNT) = REM_NUM;
359  6                        DIAG_REMS.COUNT = DIAG_REMS.COUNT + 1;
360  6                     END;
361  5                  ELSE
                           DO;
362  6                        SUBCASE_REMS.REM_NUM(SUBCASE_REMS.COUNT) = REM_NUM;
363  6                        SUBCASE_REMS.COUNT = SUBCASE_REMS.COUNT + 1;
364  6                     END;
365  5               END;
366  4            HOLD = SHL(HOLD, 1);
367  4         END BIT$LOOP;
368  3      END BYTE$LOOP;

369  2    END$PROC EXTRACT_REM_NUMS;

$EJECT

/*******************************************************************
*
*  Name: EXCLUDED
*
*  Function: Determines whether the assay results are in an exclusion domain
*            for a given reminder.
*
*  Parameters: N - the reminder number.
*              WHICH_CII_P - ptr to structure telling which cii the assay
```

```
                    *                         result is in for each parameter.
                    *
                    * Returns: TRUE if the reminder is to be excluded, else FALSE.
                    *
                    * Globals: References NULLS. Modifies none.
                    *
                    *****************************************************************/
370  1      EXCLUDED: FUNCT (N, WHICH_CII_P) BYTE;
371  2         DCL N                    BYTE;
372  2         DCL WHICH_CII_P          PTR;
373  2         DCL WHICH_CII BASED WHICH_CII_P STRUCTURE (H BYTE, P BYTE, G BYTE, L BYTE);

374  2         DCL I       BYTE;

375  2         DO I = 0 TO TOTAL_NUM_NULLS;
376  3            IF (NULLS(I).REM_NUM = N) AND
                      (NULLS(I).H_LO <= WHICH_CII.H) AND (WHICH_CII.H <= NULLS(I).H_HI) AND
                      (NULLS(I).P_LO <= WHICH_CII.P) AND (WHICH_CII.P <= NULLS(I).P_HI) AND
                      (NULLS(I).G_LO <= WHICH_CII.G) AND (WHICH_CII.G <= NULLS(I).G_HI) AND
                      (NULLS(I).L_LO <= WHICH_CII.L) AND (WHICH_CII.L <= NULLS(I).L_HI)
377  3               THEN RETURN TRUE;
378  3         END;
379  2         RETURN FALSE;

380  2      ENDSFUNCT EXCLUDED;

$EJECT

/****************************************************************
            *
            * Name: COMPUTE_PARAM_WTS
            *
            * Function: Associate a weight with each QBC parameter, based on its
            *           distance from normal weighted by a tie-breaking factor.
            *           This influences the order in which reminders are printed.
            *
            * Parameters: CII_P - Addr of structure telling which cii each param is in.
            *             PARAM_WT_P - Addr of structure that will hold the weights.
            *
            * Returns: Nothing. Side-effects the structure referenced by PARAM_WT_P.
            *
            * Globals: Modifies none. References DESCRIPTOR_WT, TIE_BREAKER_WT,
            *                         H_CII_MAP and the other 3 cii maps.
            *
            *****************************************************************/
381  1      COMPUTE_PARAM_WTS: PROC (CII_P, PARAM_WT_P);
382  2         DCL CII_P       PTR;
383  2         DCL WHICH_CII   BASED CII_P STRUCTURE (H BYTE, P BYTE, G BYTE, L BYTE);
384  2         DCL PARAM_WT_P  PTR;
385  2         DCL PARAM_WT    BASED PARAM_WT_P STRUCTURE
                               (H FLOAT$NUM, P FLOAT$NUM, G FLOAT$NUM, L FLOAT$NUM);

386  2         DCL TMP_FLOAT FLOAT$NUM;

/* first get numbers based on just the distance of each param from normal */
387  2         FLOAT$INT(DESCRIPTOR_WT(H_CII_MAP(WHICH_CII.H)), .PARAM_WT.H);
388  2         FLOAT$INT(DESCRIPTOR_WT(P_CII_MAP(WHICH_CII.P)), .PARAM_WT.P);
389  2         FLOAT$INT(DESCRIPTOR_WT(G_CII_MAP(WHICH_CII.G)), .PARAM_WT.G);
390  2         FLOAT$INT(DESCRIPTOR_WT(L_CII_MAP(WHICH_CII.L)), .PARAM_WT.L);

/* now multiply by tie-breaking factors */
391  2         STORE$CONST(@TIE_BREAKER_WT.H, @TMP_FLOAT);
392  2         MUL(.TMP_FLOAT, .PARAM_WT.H);
393  2         STORE$CONST(@TIE_BREAKER_WT.P, @TMP_FLOAT);
394  2         MUL(.TMP_FLOAT, .PARAM_WT.P);
395  2         STORE$CONST(@TIE_BREAKER_WT.G, @TMP_FLOAT);
```

```
396  2        MUL(.TMP_FLOAT, .PARAM_WT.G);
397  2        STORE$CONST(@TIE_BREAKER_WT.L, @TMP_FLOAT);
398  2        MUL(.TMP_FLOAT, .PARAM_WT.L);

399  2      END$PROC COMPUTE_PARAM_WTS;

$EJECT

/***************************************************************
             *
             * Name: ORDER_REMS
             *
             * Function: Outputs a set of reminders, in decreasing order by
             *           weight, to the Expert Interface Block.
             *
             * Parameters:
             *    REM_P - ptr to a structure holding the number of reminders of
             *            some type (hematological or diagnostic) and an array
             *            of the reminder numbers.
             *    SUBCASE_REM_P - ptr to a similar structure for subcase-type
             *                    reminders.
             *    PARAM_WT_P - ptr to a structure holding weights of each of the
             *                 four parameters, already multiplied by the
             *                 tie-breaker factors.
             *
             * Returns: Nothing. Puts the sorted reminders in EIP$INT$BLK.
             *
             * Globals: References REM_TYPE.
             *          Modifies EIP$INT$BLK and NEXT_MSG.
             *
             ***************************************************************/
400  1      ORDER_REMS: PROC (REM_P, SUBCASE_REM_P, PARAM_WT_P);
401  2        DCL (REM_P, SUBCASE_REM_P, PARAM_WT_P) PTR;
402  2        DCL REM   BASED REM_P STRUCTURE
                    (COUNT BYTE, REM_NUM(MAX_REMS_ONE_ASSAY) BYTE);
403  2        DCL SUBCASE_REM  BASED SUBCASE_REM_P STRUCTURE
                    (COUNT BYTE, REM_NUM(MAX_REMS_ONE_ASSAY) BYTE);
404  2        DCL PARAM_WT  BASED PARAM_WT_P STRUCTURE
                    (H FLOAT$NUM, P FLOAT$NUM, G FLOAT$NUM, L FLOAT$NUM);

405  2        DCL REM_WT              (MAX_REMS_ONE_ASSAY) STRUCTURE (WT FLOAT$NUM);
                    /* REM_WT(K).WT will be the weight of reminder REM.REM_NUM(K) */
406  2        DCL TMP$FLOAT           FLOAT$NUM;
407  2        DCL (I, J, D_F, MAX_OFFSET)  BYTE;
408  2        DCL FP0                 FLOAT$CONST (0.0);

/* set rem_wt as in declaration comment */
409  2        IF REM.COUNT > 0 THEN
410  2          DO I = 0 TO REM.COUNT - 1;
411  3            STORE$CONST(@FP0, @REM_WT(I).WT);
412  3            D_F = DOMINANT_FACTORS(REM.REM_NUM(I));
413  3            IF ((D_F AND H_MASK) <> 0) THEN ADD(.PARAM_WT.H, .REM_WT(I).WT);
415  3            IF ((D_F AND P_MASK) <> 0) THEN ADD(.PARAM_WT.P, .REM_WT(I).WT);
417  3            IF ((D_F AND G_MASK) <> 0) THEN ADD(.PARAM_WT.G, .REM_WT(I).WT);
419  3            IF ((D_F AND L_MASK) <> 0) THEN ADD(.PARAM_WT.L, .REM_WT(I).WT);
421  3          END;

/* next part is like a selection sort, except call OUTPUT_STRING for */
              /* each selected reminder */
422  2        IF REM.COUNT > 0 THEN
423  2          SORT_AND_OUTPUT: DO I = 0 TO REM.COUNT - 1;
424  3            MAX_OFFSET = I;
425  3            DO J = (I + 1) TO (REM.COUNT - 1);
426  4              IF GREATERTHAN(.REM_WT(J).WT, .REM_WT(MAX_OFFSET).WT) THEN
427  4                MAX_OFFSET = J;
428  4            END;
```

```
429  3              /* output reminder with next highest weight */
                    CALL OUTPUT_STRING(REM_ADDRESS(REM.REM_NUM(MAX_OFFSET)));

/* see if there's a subcase reminder that goes here */
430  3              IF SUBCASE_REM.COUNT > 0 THEN
431  3                  DO J = 0 TO SUBCASE_REM.COUNT - 1;
432  4                      IF REM_TYPE(SUBCASE_REM.REM_NUM(J)) = REM.REM_NUM(MAX_OFFSET) THEN
433  4                          DO;
434  5                              CALL OUTPUT_STRING(REM_ADDRESS(SUBCASE_REM.REM_NUM(J)));
435  5                          END;
436  4                  END;

/* put info for I'th reminder where we'll find it next time thru */
437  3              STORE(.REM_WT(I), .REM_WT(MAX_OFFSET));
438  3              REM.REM_NUM(MAX_OFFSET) = REM.REM_NUM(I);
439  3          END SORT_AND_OUTPUT;

440  2      END$PROC ORDER_REMS;

$EJECT

/*****************************************************************
          *
          * Name: EXPERT$SYSTEM
          *
          * Function: Expert interpretation of a QBC tube assay.
          *
          * Parameters: QBC_PTR - pointer to the structure where the QBC results
          *                      are stored in floating point format.
          *
          * Returns: the number of message strings to be printed.
          *
          * Globals affected: EXP$INT$BLK - the expert interface block. If
          *                   EXPERT$SYSTEM returns k, then the first k positions
          *                   (zero-based) of EXP$INT$BLK hold ptrs to strings to
          *                   be printed.
          *
          *****************************************************************/
441  1   EXPERT$SYSTEM: FUNCT(QBC_PTR) BYTE PUBLIC;
442  2       DCL QBC_PTR PTR;
443  2       DCL QBC_RSLT BASED QBC_PTR STRUCTURE (H FLOAT$NUM, P FLOAT$NUM,
                                                  G FLOAT$NUM, L FLOAT$NUM);

444  2       DCL WHICH_CII STRUCTURE (H BYTE, P BYTE, G BYTE, L BYTE);
                 /* which clinically important interval the
                    assay result for each qbc parameter lies in */

445  2       DCL ANDED_REM_BITS (NUM_REM_BYTES) BYTE;
                 /* logical and of the reminder-set bitstrings for the
                    indiv. params.*/

446  2       DCL PARAM_WT STRUCTURE (H FLOAT$NUM, P FLOAT$NUM,
                                     G FLOAT$NUM, L FLOAT$NUM);
                 /* weights of the QBC parameters, to influence order of
                    printing reminders */

447  2       DCL HEMAT_REMS   STRUCTURE (COUNT BYTE, REM_NUM(MAX_REMS_ONE_ASSAY) BYTE);
448  2       DCL DIAG_REMS    STRUCTURE (COUNT BYTE, REM_NUM(MAX_REMS_ONE_ASSAY) BYTE);
449  2       DCL SUBCASE_REMS STRUCTURE (COUNT BYTE, REM_NUM(MAX_REMS_ONE_ASSAY) BYTE);
                 /* applicable reminders of the different types, for this assay */

450  2       DCL REM_WT (MAX_REMS_ONE_ASSAY) STRUCTURE (WT FLOAT$NUM);
                 /* reminder wts -- since a float$num is an array, you can't
                    have an array of them, hence the structure */
```

```
451  2        DCL I BYTE;
452  2        DCL NUM_MSGS BYTE;

453  2        NEXT_MSG = 0;

/* round the results, as specified by Dr. Levine */
454  2        STORE(.QBC_RSLT.H, .ROUNDED_QBC_RSLT.H);
455  2        STORE(.QBC_RSLT.P, .ROUNDED_QBC_RSLT.P);
456  2        STORE(.QBC_RSLT.G, .ROUNDED_QBC_RSLT.G);
457  2        STORE(.QBC_RSLT.L, .ROUNDED_QBC_RSLT.L);
458  2        CALL ROUND(.ROUNDED_QBC_RSLT.H, H_DEC_DIGITS);
459  2        CALL ROUND(.ROUNDED_QBC_RSLT.P, P_DEC_DIGITS);
460  2        CALL ROUND(.ROUNDED_QBC_RSLT.G, G_DEC_DIGITS);
461  2        CALL ROUND(.ROUNDED_QBC_RSLT.L, L_DEC_DIGITS);

/* now map them to cii intervals */
462  2        WHICH_CII.H = GET_INTERVAL(.ROUNDED_QBC_RSLT.H, @H_CII_BOUNDS, NUM_H_CIIS);
463  2        WHICH_CII.P = GET_INTERVAL(.ROUNDED_QBC_RSLT.P, @P_CII_BOUNDS, NUM_P_CIIS);
464  2        WHICH_CII.G = GET_INTERVAL(.ROUNDED_QBC_RSLT.G, @G_CII_BOUNDS, NUM_G_CIIS);
465  2        WHICH_CII.L = GET_INTERVAL(.ROUNDED_QBC_RSLT.L, @L_CII_BOUNDS, NUM_L_CIIS);

/* output assay results and descriptors */
466  2        CALL OUTPUT_STRING(.TITLE1);
467  2        CALL OUTPUT_STRING(.TITLE2);
468  2        CALL OUTPUT_STRING(.TITLE3);
469  2        CALL OUTPUT_SIMPLE_STUFF(QBC_PTR, .WHICH_CII);

/* determine the applicable reminders, according to reminder-type */
470  2        CALL AND_REMINDERS(@H_CII(WHICH_CII.H).BITS,
                                 @P_CII(WHICH_CII.P).BITS,
                                 @G_CII(WHICH_CII.G).BITS,
                                 @L_CII(WHICH_CII.L).BITS,
                                 @ANDED_REM_BITS);
471  2        CALL EXTRACT_REM_NUMS(.ANDED_REM_BITS,
                          .HEMAT_REMS, .DIAG_REMS, .SUBCASE_REMS, .WHICH_CII);

/* output reminders, first hematological, then diagnostic, and sorted
                       according to Dr. Levine's weighting scheme within each type */
472  2        CALL COMPUTE_PARAM_WTS(.WHICH_CII, .PARAM_WT);

473  2        CALL OUTPUT_STRING(.(LF,LF,END$OF$MSG));       /* hematological */
474  2        CALL OUTPUT_STRING(.HEMAT_HEADER);
475  2        CALL ORDER_REMS(.HEMAT_REMS, .SUBCASE_REMS, .PARAM_WT);

476  2        CALL OUTPUT_STRING(.(LF,END$OF$MSG));          /* diagnostic */
477  2        CALL OUTPUT_STRING(.DIAG_HEADER);
478  2        CALL ORDER_REMS(.DIAG_REMS, .SUBCASE_REMS, .PARAM_WT);
479  2        IF DIAG_REMS.COUNT = 0 THEN    /* if no diagnostic interpretation */
480  2           CALL OUTPUT_STRING(.NO_DIAG);

/* disclaimer, copyright */
481  2        CALL OUTPUT_STRING(.(LF,LF,END$OF$MSG));
482  2        CALL OUTPUT_STRING(.DISCLAIMER);
483  2        CALL OUTPUT_STRING(.COPYRIGHT);
484  2        CALL OUTPUT_STRING(.(FF,END$OF$MSG));

485  2        RETURN NEXT_MSG;

486  2        END$FUNCT EXPERT$SYSTEM;

487  1     END$MODULE EXPERT$SYSTEM;

MODULE INFORMATION:
```

```
CODE AREA SIZE      = 09F9H   2553D
CONSTANT AREA SIZE  = 0037H    55D
VARIABLE AREA SIZE  = 018DH   397D
MAXIMUM STACK SIZE  = 0020H    32D
1131 LINES READ
0 PROGRAM WARNINGS
0 PROGRAM ERRORS
```

DICTIONARY SUMMARY:

```
347KB MEMORY AVAILABLE
20KB MEMORY USED  (5%)
0KB DISK SPACE USED
```

END OF PL/M-86 COMPILATION

```
Line#  Source Line                    Microsoft C Compiler Version 4.00

1   /****************************************************************
  2   ** plmsg.c -- This file is part of the update program for the QBC
  3   **            Hematology Expert System. The only externally-called
  4   **            function is plmsg, which generates the PL/M module that
  5   **            declares the texts of the reminder messages.  This is
  6   **            MSGOUT in update.h.
  7   **            Returns ERR if can't open a msg file for an existing
  8   **            reminder, or can't read it.
  9   **
 10   **    Joan Curry
 11   **    Becton Dickinson Research Center
 12   **    November 22, 1986
 13   *****************************************************************/
 14
 15   #include <stdio.h>
 16   #include <string.h>
 17   #include <stdlib.h>
 18   #include <ctype.h>
 19   #include <time.h>
 20   #include "update.h"
 21
 22   #define TITLE "$TITLE(' QBC-III EXPERT SYSTEM, MESSAGE MODULE ')\n\n"
 23   #define SUBJECT "\t* THIS MODULE CONTAINS THE REGULAR REMINDER MESSAGES FOR THE QBC\n\
 24   \t* EXPERT SYSTEM.  SPECIAL MESSAGES, SUCH AS THE DISCLAIMER AND\n\
 25   \t* NO_DIAGNOSIS MESSAGE ARE IN A DIFFERENT FILE.\n"
 26
 27   /* external functions */
 28   extern FILE    *write_open(char*);
 29   extern FILE    *read_open(char*);
 30   extern void     perror(char*);
 31   extern char    *ctime(long*);
 32   extern long     time(long*);
 33   extern int      check_continue(void);
 34
 35   /* external variables -- referenced but none modified */
 36   extern int      highest_rem_num;
 37   extern char    *rem_exists;
 38   extern char    *rem_type;
 39   extern char    *pcflag;
 40   extern char    *inclits;
 41   extern char    *start_stars;
 42   extern char    *comment_skip;
 43   extern char    *blurb;
 44   extern char    *end_stars;
 45
 46   /* local functions */
 47   static int      all_blank(char*);
 48   static char    *skip_junk(FILE*, char*, int);
```

```
49
50   /****************************************************************
51   **    plmmsg
52   **
53   **    ... see header documentation
54   */
55   int plmsg()
56   {
57           FILE    **fpout, **fpin;
58           long    timenum;
59           int     i, j,
60                   blankflag;
61           char    path[38],
62                   line[LINE_LEN_PLUS1],
63                   errbuff[41],
64                   numbuff[8];
65           char    *p, *here, *first, *last, *more;
66
67           fpout = write_open(MSGOUT);
68           if (fpout == NULL)
69                   return(ERR);
70
71           (void) fputs(TITLE, fpout);
72           (void) fputs(pcflag, fpout);
73           (void) fputs("EXPMSG: DO;\n", fpout);
74           (void) fputs(inclits, fpout);
75           (void) fputs(start_stars, fpout);
76           (void) fputs("\t*\t\t@QBC EXPERT SYSTEM REMINDER MESSAGE MODULE\n", fpout);
77           (void) fputs(comment_skip, fpout);
78           (void) fputs(SUBJECT, fpout);
79           (void) fputs(comment_skip, fpout);
80           (void) fputs(blurb, fpout);
81           (void) fputs(comment_skip, fpout);
82           (void) fputs("\t*  ", fpout);
83           (void) time(&timenum);
84           (void) fputs(ctime(&timenum), fpout);
85           (void) fputs(comment_skip, fpout);
86           (void) fputs(end_stars, fpout);
87           (void) fputs("$EJECT\n\n", fpout);
88
89           (void) strcpy(path, MSGDIR);
90           for (here = path; *here != '\0'; here++)
91                   ;       /* find where the directory name ends */
92           *here++ = '\\';
93           *here++ = 'r';
94
95           for (i = 0; i <= highest_rem_num; i++) {
96                   (void) itoa(i, here, 10);
97
98                   if (!rem_exists[i]) { /* have to have something to initialize ptr to */
99                           (void) fprintf(fpout, "DCL MXs(*) BYTE DATA\n", here);
100                          (void) fprintf(fpout, "(SBF,'INTERNAL ERROR: CONTACT TECHNICAL SUPPORT',");
101                          (void) fprintf(fpout, "EBF,CR,LF,LF,SHORT$MSG$END,END$OF$MSG);\n\n");
102                          continue;
103                  }
104
105                  if ((fpin = read_open(path)) == NULL) {
106                          return(ERR);
107                  }
108
109                  if ((more = skip_junk(fpin, line, LINE_LEN_PLUS1)) == NULL) {
110                          (void) sprintf(errbuff, "Error: %s is empty or IO error", path);
111                          perror(errbuff);
112                          (void) fclose(fpin);
113                          return(ERR);
114                  }
115
```

```
116                    (void) fprintf(fpout, "DCL M%s(*) BYTE DATA\n", here);
117                    if (rem_type[i] >= 0) {                  /* subcase reminder */
118                            (void) fputs(" (SHORT$MSG$END,", fpout);
119                    }
120                    else {                                    /* not subcase */
121                            for (first = line; isspace(*first); first++)
122                                    ;       /* find first non-blank char */
123                            for (last = line + strlen(line) - 1; isspace(*last); last--)
124                                    ;       /* and last non-blank char */
125                            (void) fputs("(SBF, ' ", fpout);
126                            for (p = first; p <= last; p++) {
127                                    if (*p == '\'')
128                                            (void) putc('\'', fpout);
129                                    (void) putc(toupper(*p), fpout);
130                            }
131                            if (*--p != '.')
132                                    (void) putc('.', fpout);
133                            (void) fputs("',\n  EBF,CR,LF,LF,SHORT$MSG$END,", fpout);
134                            more = skip_junk(fpin, line, LINE_LEN_PLUS1);
135                    }
136                    blankflag = 0;
137                    while (more != NULL) {
138                            if (all_blank(line))
139                                    blankflag = 1;
140                            else {
141                                    if (blankflag) {
142                                            fputs("LF,", fpout);
143                                            blankflag = 0;
144                                    }
145                                    (void) fputs("\n'", fpout);
146                                    for (last = line + strlen(line) - 1; isspace(*last); last--)
147                                            ; /* find last non-blank char */
148                                    for (p = line; p <= last; p++) {
149                                            if (*p == '\'')
150                                                    (void) putc('\'', fpout);
151                                            (void) putc(*p, fpout);
152                                    }
153                                    (void) fputs("',CR,LF,", fpout);
154                            }
155                            more = fgets(line, LINE_LEN_PLUS1, fpin);
156                    }
157                    (void) fputs("LF,END$OF$MSG);\n\n\n", fpout);
158                    (void) fclose(fpin);
159            }
160
161            /* do decl of addresses of reminders */
162            (void) fputs("DCL REM_ADDRESS (TOTAL_NUM_REMS) PTR PUBLIC DATA\n\t(", fpout);
163            j = 1;
164            for (i = 0; i <= highest_rem_num; i++) {
165                    (void) fprintf(fpout, ".M%s", itoa(i, numbuff, 10));
166                    if (i == highest_rem_num)
167                            (void) fputs(");\n\n", fpout);
168                    else if (j == 10) {
169                            (void) fputs(",\n\t ", fpout);
170                            j = 1;
171                    }
172                    else {
173                            (void) fputs(", ", fpout);
174                            j += 1;
175                    }
176            }
177            (void) fputs("END$MODULE EIPMSG;\n", fpout);
178            (void) fclose(fpout);
179            return(OK);
``` plmsg Local Symbols

| Name | Class | Offset | Register |
|---|---|---|---|
| fpout . . . . . . . . . . . . . . . . | auto | -00ba | |
| timenum . . . . . . . . . . . . . . . | auto | -00b8 | |
| j . . . . . . . . . . . . . . . . . | auto | -00b4 | |
| numbuff . . . . . . . . . . . . . . | auto | -00b2 | |
| last . . . . . . . . . . . . . . . . | auto | -00aa | |
| i . . . . . . . . . . . . . . . . . | auto | -00a8 | |
| blankflag . . . . . . . . . . . . . | auto | -00a6 | |
| line . . . . . . . . . . . . . . . . | auto | -00a4 | |
| more . . . . . . . . . . . . . . . . | auto | -0052 | |
| p . . . . . . . . . . . . . . . . . | auto | -0050 | |
| here . . . . . . . . . . . . . . . . | auto | -004e | |
| first . . . . . . . . . . . . . . . | auto | -004c | |
| fpin . . . . . . . . . . . . . . . . | auto | -004a | |
| path . . . . . . . . . . . . . . . . | auto | -0048 | |
| errbuff . . . . . . . . . . . . . . | auto | -002a | |

```
180     }
181
182     /************************************************************
183     **      all_blank
184     **
185     **      1 if s is NULL or if the string referenced by s has only blanks, tabs,
186     **      and newlines.
187     **
188     */
189     static int all_blank(s)
190     char    *s;
191     {
192             if (s == NULL)
193                     return(1);
194             else {
195                     while (isspace(*s))
196                             s++;
197                     return(*s == '\0');
``` all_blank Local Symbols

| Name | Class | Offset | Register |
|---|---|---|---|
| s . . . . . . . . . . . . . . . . . | param | 0004 | |

```
198     }
199     }
200
201     /************************************************************
202     **      skip_junk
203     **
204     **      Skips over any blank lines in fp, and puts the first non-blank line
205     **      into "line". Length of "line" should be >= n, and length of input
206     **      line should be <= n-1. If it isn't, only the first n-1 chars are
207     **      read, and a '\0' is added to the end of that. If a newline is read,
208     **      it does not get put into "line". If end of file is reached before
209     **      a non-blank line, "line" will be "".
210     */
211     static char *skip_junk(fp, line, n)
212     FILE    **fp;
213     char    *line;
214     int     n;
215     {
216             char    *rslt;
217
218             rslt = fgets(line, n, fp);
219             while (rslt != NULL && all_blank(line))
220                     rslt = fgets(line, n, fp);
221             if (rslt == NULL)
```

```
222              *line = '\0';
223          return(rslt);
``` skip_junk - Local Symbols

| Name | Class | Offset | Register |
|---|---|---|---|
| rslt............. | auto | -0002 | |
| *p............... | param | 0004 | |
| line............. | param | 0006 | |
| n................ | param | 0008 | |

```
224 }
```

Global Symbols

| Name | Type | Size | Class | Offset |
|---|---|---|---|---|
| _ctype............ | struct/array | *** | extern | *** |
| _flsbuf........... | near function | *** | extern | *** |
| all_blank......... | near function | *** | static | 052e |
| blurb............. | near pointer | 2 | extern | *** |
| comment_skip...... | near pointer | 2 | extern | *** |
| ctime............. | near function | *** | extern | *** |
| end_stars......... | near pointer | 2 | extern | *** |
| fclose............ | near function | *** | extern | *** |
| fgets............. | near function | *** | extern | *** |
| fprintf........... | near function | *** | extern | *** |
| fputs............. | near function | *** | extern | *** |
| highest_rea_num... | int | 2 | extern | *** |
| inclits........... | near pointer | 2 | extern | *** |
| itoa.............. | near function | *** | extern | *** |
| pcflag............ | near pointer | 2 | extern | *** |
| perror............ | near function | *** | extern | *** |
| pimsg............. | near function | *** | global | 0000 |
| read_open......... | near function | *** | extern | *** |
| rem_exists........ | near pointer | 2 | extern | *** |
| rem_type.......... | near pointer | 2 | extern | *** |
| skip_junk......... | near function | *** | static | 0561 |
| sprintf........... | near function | *** | extern | *** |
| start_stars....... | near pointer | 2 | extern | *** |
| strcpy............ | near function | *** | extern | *** |
| strlen............ | near function | *** | extern | *** |
| time.............. | near function | *** | extern | *** |
| write_open........ | near function | *** | extern | *** |

Code size = 05a0 (1440)
Data size = 02a8 (680)
Bss size  = 0000 (0)

No errors detected

Microsoft C Compiler Version 4.00

Line#  Source Line

```
   1  /************************************************************
   2  ** pldata.c --       This file is part of the update program for the BDC
   3  **          Hematology Expert System. The only externally-called
   4  **          function is pldata, which generates the PL/M module that
   5  **          declares the bitstrings for the applicable reminders, the
   6  **          structure for the null domains, and the reminder types and
   7  **          dominant factors. This is DATAOUT in update.h.
   8  **          Returns ERR if it couldn't open DATAOUT, else OK.
   9  **  Joan Curry
  10  **  Becton Dickinson Research Center
  11  **  November 22, 1986
```

```
12   *************************************************************/
13
14   #include <stdio.h>
15   #include <string.h>
16   #include <stdlib.h>
17   #include <ctype.h>
18   #include <time.h>
19   #include "update.h"
20
21   #define TITLE "$TITLE(' OBC-III EXPERT SYSTEM, SECOND DATA MODULE ')\n\n"
22   #define SUBJECT "\t* THIS MODULE CONTAINS THE DATA DECLARATIONS FOR THE BITSTRINGS\n\
23   \t* REPRESENTING APPLICABLE REMINDERS, THE STRUCTURES FOR THE NULL\n\
24   \t* DOMAINS, AND THE ARRAYS OF DOMINANT FACTORS AND REMINDER TYPES.\n"
25
26   /* external functions */
27   extern FILE              *write_open(char*);
28   extern char              *ctime(long*);
29   extern long              time(long*);
30
31   /* external variables -- referenced but none modified */
32   extern struct charpp_struct   applic_rems;
33   extern int                    highest_rem_num;
34   extern char                   *rem_type;
35   extern unsigned char          *dom;
36   extern struct cii_domain      cii_extent;
37   extern int                    num_rem_bytes;
38   extern struct null_struct     nulls;
39   extern int                    total_num_nulls;
40
41   extern char              *pcflag;
42   extern char              *inclits;
43   extern char              *start_stars;
44   extern char              *comment_skip;
45   extern char              *blurb;
46   extern char              *end_stars;
47
48   /* local functions */
49   static void put_rem_bits(FILE*, char**, int);
50   static void put_nulls(FILE*);
51   static void put_rem_types(FILE*);
52   static void put_dom(FILE*);
53
54   /******************************************************************
55   **     p2data
56   **
57   **     ... see header documentation
58   */
59   int p2data()
60   {
61        FILE    *fp;
62        long    timenum;
63
64        if ((fp = write_open(DATAOUT)) == NULL)
65                return(ERR);
66
67        (void) fputs(TITLE, fp);
68        (void) fputs(pcflag, fp);
69        (void) fputs("EXPDATA2: DO;\n", fp);
70        (void) fputs(inclits, fp);
71        (void) fputs(start_stars, fp);
72        (void) fputs("\t\t\tOBC EXPERT SYSTEM DATA MODULE 2\n", fp);
73        (void) fputs(comment_skip, fp);
74        (void) fputs(SUBJECT, fp);
75        (void) fputs(comment_skip, fp);
76        (void) fputs(blurb, fp);
77        (void) fputs(comment_skip, fp);
78        (void) fputs("\t* ", fp);
79        (void) time(&timenum);
```

```
 80         (void) fputs(ctime(&timenum), fp);
 81         (void) fputs(comment_skip, fp);
 82         (void) fputs(end_stars, fp);
 83         (void) fputs("$EJECT\n\n", fp);
 84
 85         (void) fputs("DCL H_CII (NUM_H_CIIS) STRUCTURE (BITS (NUM_REM_BYTES) BYTE) PUBLIC DATA\n", fp);
 86         put_rem_bits(fp, applic_rems.h, cii_extent.h.ub);
 87
 88         (void) fputs("DCL P_CII (NUM_P_CIIS) STRUCTURE (BITS (NUM_REM_BYTES) BYTE) PUBLIC DATA\n", fp);
 89         put_rem_bits(fp, applic_rems.p, cii_extent.p.ub);
 90
 91         (void) fputs("DCL G_CII (NUM_G_CIIS) STRUCTURE (BITS (NUM_REM_BYTES) BYTE) PUBLIC DATA\n", fp);
 92         put_rem_bits(fp, applic_rems.g, cii_extent.g.ub);
 93
 94         (void) fputs("DCL L_CII (NUM_L_CIIS) STRUCTURE (BITS (NUM_REM_BYTES) BYTE) PUBLIC DATA\n", fp);
 95         put_rem_bits(fp, applic_rems.l, cii_extent.l.ub);
 96
 97         put_nulls(fp);
 98
 99         put_rem_types(fp);
100
101         put_doa(fp);
102
103         (void) fputs("END$MODULE EIPDATA2;\n", fp);
104         (void) fclose(fp);
105         return(OK);
``` pledata Local Symbols

Line# Source Line                    Microsoft C Compiler Version 4.00

| Name | Class | Offset | Register |
|---|---|---|---|
| timenum | auto | -0006 | |
| fp | auto | -0002 | |

```
106 }
107
108 /**********************************************************************
109 **    put_rem_bits
110 **
111 **    Writes the declaration of the bitstrings representing the applicable
112 **    reminders for one QBC parameter (but not the "DCL ..." line).
113 */
114 static void put_rem_bits(fp, a, num_ciis)
115 FILE  *fp;
116 char  **a;
117 int   num_ciis;
118 {
119     char  **cii, **lastcii;
120     char  *rem, *lastrem;
121     int   bit;
122     int   num_rems;
123
124     (void) fputs(" (", fp);
125     num_rems = 8 * num_rem_bytes;   /* have to have even # of bytes */
126
127     lastcii = a + num_ciis - 1;
128     for (cii = a; cii <= lastcii; cii++) {
129         lastrem = *cii + num_rems - 1;
130         bit = 0;
131         for (rem = *cii; rem <= lastrem; rem++) {
132             (void) putc(*rem, fp);
133             if (bit == 7) {
134                 if (cii == lastcii && rem == lastrem)
135                     (void) fputs("B);\n\n", fp);
136                 else if (rem == lastrem) {
137                     (void) fputs("B,\n ", fp);
```

```
138                                       )
139                                  else {
140                                       (void) fputs("B,", fp);
141                                  }
142                                  bit = 0;
143                             }
144                        else bit++;
145                   }
146        }
147  }
``` put_rem_bits Local Symbols

| Name | Class | Offset | Register |
|---|---|---|---|
| lastcii . . . . . . . . . . . . . . auto | | -000c | |
| rem . . . . . . . . . . . . . . . . auto | | -000a | |
| cii . . . . . . . . . . . . . . . . auto | | -0008 | |
| lastrem . . . . . . . . . . . . . auto | | -0006 | |
| num_rems. . . . . . . . . . . . . auto | | -0004 | |
| bit . . . . . . . . . . . . . . . . auto | | -0002 | |
| fp. . . . . . . . . . . . . . . . . param | | 0004 | |
| a . . . . . . . . . . . . . . . . . param | | 0006 | |
| num_ciis. . . . . . . . . . . . . param | | 0008 | |

```
148
149  /****************************************************************
150  **   put_nulls
151  **
152  **   Writes the data declaration of the PL/M representation of the "nulls",
153  **   or exclusion domains. Here we convert from the 1-based domains of the
154  **   kb file and the nulls struct, to the 0-based domains of the PL/M program.
155  */
156  static void put_nulls(fp)
157  FILE    *fp;
158  {
159        struct cii_domain    *p, *lastp;
160
161        (void) fputs("DCL NULLS (TOTAL_NUM_NULLS) STRUCTURE\n", fp);
162        (void) fputs(" (REM_NUM BYTE,\n  H_LO BYTE, H_HI BYTE,\n", fp);
163        (void) fputs("  P_LO BYTE, P_HI BYTE,\n  G_LO BYTE, G_HI BYTE,\n", fp);
164        (void) fputs("  L_LO BYTE, L_HI BYTE) PUBLIC DATA\n\t(", fp);
165
166        p = nulls.list;
167        lastp = p + nulls.num_nulls - 1;
168        while (p <= lastp) {
169             (void) fprintf(fp, "%4d,%4d,%4d,%4d,%4d,%4d,%4d,%4d,%4d",
170                       p->rem_num, p->h.lb-1, p->h.ub-1,
171                                   p->p.lb-1, p->p.ub-1,
172                                   p->g.lb-1, p->g.ub-1,
173                                   p->l.lb-1, p->l.ub-1 );
174             if (p == lastp)
175                  (void) fputs(");\n\n", fp);
176             else
177                  (void) fputs(",\n\t ", fp);
178             p++;
179        }
180  }
``` put_nulls Local Symbols

| Name | Class | Offset | Register |
|---|---|---|---|
| lastp . . . . . . . . . . . . . . auto | | -0004 | |
| p . . . . . . . . . . . . . . . . auto | | -0002 | |
| fp. . . . . . . . . . . . . . . . param | | 0004 | |

```
181
182  /****************************************************************
```

```
183  **    put_rem_types
184  **
185  **    Writes the PL/M declarations for the reminder types.
186  */
187  static void put_rem_types(fp)
188  FILE    *fp;
189  {
190          char    *p, *lastp;
191          int     i;
192
193          (void) fputs("DCL REM_TYPE (TOTAL_NUM_REMS) BYTE PUBLIC DATA\n (", fp);
194
195          lastp = rem_type + highest_rem_num;
196          i = 0;
197          for (p = rem_type; p <= lastp; p++) {
198                  switch (*p) {
199                          case HEMAT_TYPE:
200                                  (void) fputs(" HEMAT_TYPE", fp);
201                                  break;
202                          case DIAG_TYPE:
203                                  (void) fputs(" DIAG_TYPE ", fp);
204                                  break;
205                          default:
206                                  (void) fprintf(fp, " %-10d", (int) *p);
207                                  break;
208                  }
209                  if (p == lastp)
210                          (void) fputs(");\n\n", fp);
211                  else if (i == 9) {
212                          (void) fputs(",\n ", fp);
213                          i = 0;
214                  }
215                  else {
216                          (void) putc(',', fp);
217                          i++;
218                  }
219          }
220  }
``` put_rem_types  Local Symbols

| Name | Class | Offset | Register |
|------|-------|--------|----------|
| lastp | auto | -0006 | |
| i | auto | -0004 | |
| p | auto | -0002 | |
| fp | param | 0004 | |

```
221
222  /***********************************************************
223  **    put_dom
224  **
225  **    Writes the PL/M declaration for the dominant parameters, or factors.
226  */
227  static void put_dom(fp)
228  FILE    *fp;
229  {
230          unsigned char   *p, *lastp;
231          int             i;
232
233          (void) fputs("DCL DOMINANT_FACTORS (TOTAL_NUM_REMS) BYTE PUBLIC DATA\n (", fp);
234
235          lastp = dom + highest_rem_num;
236          i = 0;
237          for (p = dom; p <= lastp; p++) {
238                  (void) fprintf(fp, "%IIH", (unsigned int) *p);
239
240                  if (p == lastp)
```

```
241                         (void) fputs(");\n\n", fp);
242                 else if (i == 9) {
243                         (void) fputs(",\n  ", fp);
244                         i = 0;
245                 }
246                 else {
247                         (void) fputs(", ", fp);
248                         i++;
249                 }
250         }
251 }
``` put_dom Local Symbols

| Name  | Class | Offset | Register |
|-------|-------|--------|----------|
| lastp | auto  | -0006  |          |
| i     | auto  | -0004  |          |
| p     | auto  | -0002  |          |
| fp    | param | 0004   |          |

Global Symbols

| Name | Type | Size | Class | Offset |
|------|------|------|-------|--------|
| _flsbuf | near function | *** | extern | *** |
| applic_res | struct/array | 8 | extern | *** |
| blurb | near pointer | 2 | extern | *** |
| cii_extent | struct/array | 18 | extern | *** |
| comment_skip | near pointer | 2 | extern | *** |
| ctime | near function | *** | extern | *** |
| dom | near pointer | 2 | extern | *** |
| end_stars | near pointer | 2 | extern | *** |
| fclose | near function | *** | extern | *** |
| fprintf | near function | *** | extern | *** |
| fputs | near function | *** | extern | *** |
| highest_res_num | int | 2 | extern | *** |
| inclits | near pointer | 2 | extern | *** |
| nulls | struct/array | 4 | extern | *** |
| num_res_bytes | int | 2 | extern | *** |
| pcflag | near pointer | 2 | extern | *** |
| pldata | near function | *** | global | 0000 |
| pmdata | near function | *** | static | 03f4 |
| put_dom | near function | *** | static | 027b |
| put_nulls | near function | *** | static | 01a2 |
| put_res_bits | near function | *** | static | 032d |
| put_res_types | near function | *** | static | *** |
| res_type | near pointer | 2 | extern | *** |
| start_stars | near pointer | 2 | extern | *** |
| time | near function | *** | extern | *** |
| write_open | near function | *** | extern | *** |

Code size = 047f (1151)
Data size = 0421 (1057)
Bss size  = 0000 (0)

No errors detected

Physician's Diagnostic Reminders
QBC Centrifugal Hematology System

Written By: Robert A. Levine, M.D.
Edited By: Maxwell M. Wintrobe, M.D.

```
Hematocrit (%)                 =    15.0    extremely decreased

Platelets (x10^9/L)            =    23      extremely decreased

Total WBC (x10^9/L)            =    0.7

Percent Granulocytes         =    57
  Granulocytes (x10^9/L)       =    0.4     extremely decreased Percent Lymphs+Monos         =    43
  Lymphs+Monos (x10^9/L)       =    0.3     extremely decreased
```

GENERAL HEMATOLOGIC CLINICAL REMINDERS:

ANEMIA.

SEVERE GRANULOCYTOPENIA.

LYMPHOCYTOPENIA.

SPECIFIC DIAGNOSTIC CONSIDERATIONS INCLUDE:

OMISSION OF FLOAT/INCORRECT FILLING/LEAKAGE.

```
Hematocrit (%)                 =    15.0    extremely decreased

Platelets (x10^9/L)            =    23      extremely decreased

Total WBC (x10^9/L)            =    0.7

Percent Granulocytes         =    57
  Granulocytes (x10^9/L)       =    0.4     extremely decreased Percent Lymphs+Monos         =    43
  Lymphs+Monos (x10^9/L)       =    0.3     extremely decreased
```

GENERAL HEMATOLOGIC CLINICAL REMINDERS:

ANEMIA.

Hematocrit values that are below normal signal anemia. Anemia can be due to (a) acute or chronic blood loss, (b) decreased red cell production, caused by infection or inflammation, hypoplasia, neoplasm, or nutritional deficiency, (c) increased red cell destruction\hemolytic anemia. The nature and cause of the anemia should be determined. Suggested additional tests include an examination of the peripheral smear and determination of red blood cell indices as well as a reticulocyte count. Additional tests may include testing the stool for the presence of occult blood and parasites, as well as determination of the total and fractionated serum bilirubin and urinary evidences of hemoglobin breakdown. Wintrobe, M. I.; Clinical Hematology, Ed. 8, pp. 529-558 and Table 20-1, p. 541.

Hematocrits at this level can result in significant tissue hypoxia and may be associated with signs and symptoms of cardiac failure.

SEVERE GRANULOCYTOPENIA.

Granulocyte counts of $0.5 \times 10^9/L$ or less present a great risk of infection. Their cause must be sought. Prophylactic antibiotic therapy is generally required. Severely decreased granulocyte counts may be drug induced (aminopyrine, phenothiazines, sulfonamides, antithyroids, and gold are common examples) or chemotherapy induced. Aplastic anemia also is a cause. Milder degrees of granulocytopenia may be seen in certain infections (typhoid, paratyphoid, measles, infectious hepatitis, infectious mononucleosis, malaria, brucellosis and most rickettsial diseases). Impaired production of granulocytes may be due to megaloblastic anemia, especially pernicious anemia. Cachexia or debilitated states, systemic lupus erythematosus, splenomegaly and anaphylaxis also are possible causes. Additional tests include those suggested by specific enquiries as to the clinical manifestations of these disorders, as well as those tests indicated by the results of the physical examination. Wintrobe, M.M.; Clinical Hematology, Ed. 8, pp.1304-1312.

| | | | |
|---|---|---|---|
| Hematocrit (%) | = | 15.0 | extremely decreased |
| Platelets ($\times 10^9/L$) | = | 23 | extremely decreased |
| Total WBC ($\times 10^9/L$) | = | 0.7 | |
| Percent Granulocytes | = | 57 | |
| Granulocytes ($\times 10^9/L$) | = | 0.4 | extremely decreased |
| Percent Lymphs+Monos | = | 43 | |
| Lymphs+Monos ($\times 10^9/L$) | = | 0.3 | extremely decreased |

GENERAL HEMATOLOGIC CLINICAL REMINDERS:

LYMPHOCYTOPENIA.

A decrease in lymphocytes/monocytes occurs in association with bacterial infections, as the result of Cushing's syndrome or corticosteroid administration, in Hodgkin's disease and as the effect of radiation or chemotherapy. It may also be seen in collagen vascular diseases and in acquired immunodeficiency syndrome (AIDS). Additional tests include examination of the peripheral smear and those appropriate to identification of the possible causes of the lymphocytopenia. Wintrobe, M.M.; Clinical Hematology, Ed. 8, p. 1304.

SPECIFIC DIAGNOSTIC CONSIDERATIONS INCLUDE:

OMISSION OF FLOAT/INCORRECT FILLING/LEAKAGE.

In cases of apparent pancytopenia, operator error such as omission of the float or blood leakage must be ruled out. Always check, prior to reading, to see that the plasma level is within the "fill lines." Wintrobe, M.M., Wardlaw, S.C., and Levine, R.A.; Quantitative Buffy Coat Analysis, a Pictorial Review and Reference Guide, copyright 1984.

The above hematologic values are also compatible with pancytopenia. Because of the proportionate decrease in the lymphocyte/monocyte layer, which is not generally seen in pancytopenia, omission of the float or incorrect filling or leakage is more likely. If repeat analysis reveals similar hematologic values, however, pancytopenia with all its implications should be considered. Wintrobe, M.M.; Clinical Hematology, Ed. 8, pp. 698-700.

Physician's Diagnostic Reminders
QBC Centrifugal Hematology System

Written By: Robert A. Levine, M.D.
Edited By: Maxwell M. Wintrobe, M.D.

| | | | |
|---|---|---|---|
| Hematocrit (%) | = | 63.8 | markedly elevated |
| Platelets (x10^9/L) | = | 18 | extremely decreased |
| Total WBC (x10^9/L) | = | 3.3 | |
| Percent Granulocytes | = | 52 | |
| Granulocytes (x10^9/L) | = | 1.7 | moderately decreased |
| Percent Lymphs+Monos | = | 48 | |
| Lymphs+Monos (x10^9/L) | = | 1.6 | slightly below normal range |

GENERAL HEMATOLOGIC CLINICAL REMINDERS:

THROMBOCYTOPENIA ASSOCIATED WITH GRANULOCYTOPENIA (BICYTOPENIA).

POLYCYTHEMIA (ERYTHROCYTOSIS).

MODERATE GRANULOCYTOPENIA.

LYMPHOCYTOPENIA.

SPECIFIC DIAGNOSTIC CONSIDERATIONS INCLUDE:

TECHNICAL ALERT. CONCENTRATED SPECIMEN. POSSIBLE IMPROPER MIXING.

| | | | |
|---|---|---|---|
| Hematocrit (%) | = | 28.2 | markedly decreased |
| Platelets (x10^9/L) | = | 77 | markedly decreased |
| Total WBC (x10^9/L) | = | 2.0 | |
| Percent Granulocytes | = | 30 | |
| Granulocytes (x10^9/L) | = | 0.6 | extremely decreased |
| Percent Lymphs+Monos | = | 70 | |
| Lymphs+Monos (x10^9/L) | = | 1.4 | slightly below normal range |

GENERAL HEMATOLOGIC CLINICAL REMINDERS:

SEVERE GRANULOCYTOPENIA.

RELATIVE LYMPHOCYTOSIS.

ANEMIA.

LYMPHOCYTOPENIA.

SPECIFIC DIAGNOSTIC CONSIDERATIONS INCLUDE:

PANCYTOPENIA.

OMISSION OF FLOAT/INCORRECT FILLING/LEAKAGE.

PRELEUKEMIA.

| | | | |
|---|---|---|---|
| Hematocrit (%) | = | 28.2 | markedly decreased |
| Platelets (x10^9/L) | = | 77 | markedly decreased |
| Total WBC (x10^9/L) | = | 2.0 | |
| Percent Granulocytes | = | 30 | |
| Granulocytes (x10^9/L) | = | 0.6 | extremely decreased |
| Percent Lymphs+Monos | = | 70 | |
| Lymphs+Monos (x10^9/L) | = | 1.4 | slightly below normal range |

TECHNICAL ALERT

POSSIBLE OMISSION OF FLOAT/INCORRECT FILLING/LEAKAGE

SPECIFIC DIAGNOSTIC CONSIDERATIONS INCLUDE:

PANCYTOPENIA.

PRELEUKEMIA.

GENERAL HEMATOLOGIC CLINICAL REMINDERS:

SEVERE GRANULOCYTOPENIA.

RELATIVE LYMPHOCYTOSIS.

ANEMIA.

LYMPHOCYTOPENIA.

What is claimed is:

1. An apparatus for the non-interactive, automatic interpretation of hematology results comprising:
   data processing means which includes;
      means for evaluating blood-derived parametric values, and
      means for ascertaining a clinically important interval (CII) combination applicable to blood-derived parametric values from a listing a plural CII's and producing output messages therefrom;
   memory means for storing data and data-processing instructions to be executed by the data processing means;
   means for entering data which represent the values of hematology parameters derived from a patient's blood; and
   means for outputting the messages of hematologic/-diagnostic significance applicable to the patient;
   wherein the memory means stores a data base and execution-instructions of an automatically interpreting hematology-diagnostic system which is suitable for operation upon the hematology parameters and their blood-derived values;
   the data base including:
      a relatively large number of messages of hematology diagnostic significance, each message being associated with a range of values for each of the hematology parameters, each range of values constituting one CII, and
      a listing of the CII's within which the blood-derived parametric values may lie, the listing including a series of consecutive CII numbers and a range of values and a descriptive phrase associated with each CII;
   the stored execution-instructions causing the data processing means to evaluate the blood-derived parametric values and to retrieve from the memory means the one or more messages whose CII combinations apply to the blood-derived parametric values, wherein the one or more messages are provided in a form to permit the interpretation of the hematologic condition of the patient.

2. The apparatus of claim 1 wherein said stored execution-instructions further include directions to
   determine applicable CIIs and associated descriptive phrases, corresponding to each one of the patient's input parametric values and prepare for output the applicable descriptive phrases.

3. The apparatus of claim 2 wherein the stored execution-instructions include further directions to the processing means to:
prepare the output for printout with, and aligned to, each applicable descriptive phrase, its associated parameter and the patient-derived value of such associated parameter; and
cause a printout, with the prepared descriptive phrase, the thereto aligned prepared items.

4. The apparatus of claim 1, wherein the parameters are hematocrit (H), platelet count (P), granulocytes (G); and lymphocyte/monocyte count (L).

5. The apparatus of claim 4 wherein hematocrit (H) is expressed in percent; and platelet count (P), granulocytes (G), lymphocyte/monocyte count (L), each is expressed in $\times 10^9$/L.

6. The apparatus of claim 1 wherein the stored data base further includes:
an individual reminder message number for, and unique to, each reminder message, the message numbers being in a sequence which runs through the hematologic reminder messages and diagnostic reminder messages.

7. The apparatus of claim 6 wherein the stored data base further includes, for each parameter, and then in turn for each CII number applicable to that parameter, an array of consecutive one-bit positions, the number of such positions in each array being in correspondence to the reminder message numbers, the arrangement being such that for each reminder message number there appears in the thereto corresponding one bit-positions—all parameters and all their respective CII numberarrays considered—a binary one in such corresponding bit-positions, for which the parameter and that parameter's CII number are applicable to the corresponding reminder message number and its reminder message, while elsewhere binary zeroes appear.

8. The apparatus of claim 1 wherein:
said data includes specialized hematogical data obtained by quantitative buffy coat analysis of blood in a sample; and
said means for outputting messages provides messages in human language.

9. An apparatus for the non-interactive, automatic interpretation of quantitative buffy coat results comprising:
data processing means which includes;
means for evaluating blood-derived parametric values, and
means for ascertaining a clinically important interval (CII) combination applicable to blood-derived parametric values from a listing a plural CII's and producing output messages therefrom;
memory means for storing data and data-processing instructions to be executed by the data processing means;
means for entering data which represent the values of hematology parameters derived from a patient's blood; and
means for outputting the messages, of hematologic/diagnostic significance, applicable to the patient;
wherein the memory means stores a data base and execution-instructions of an automatically interpreting hematology-diagnostic system which is suitable for operation upon the hematology parameters and their values as derived by quantitative buffy coat analysis;
the data base including:
a relatively large number of messages of hematologic diagnostic significance, each message being associated with a range of values for each of the hematology parameters each range of values constituting one CII, and;
a listing of the CII's within which the blood-derived parametric values may lie, the listing including a series of consecutive CII numbers and a range of values and a descriptive phrase associated with each CII;
the stored execution-instructions causing the data processing means to evaluate the blood-derived parametric values and to retrieve from the memory means the one or more messages whose CII combinations apply to the blood-derived parametric values, wherein the one or more messages are provided in a form to permit the interpretation of the hematologic condition of the patient.

10. Non-interactive hematology-diagnostic apparatus employing expert-system technology, the apparatus comprising:
a computer/data-processor which is provided with:
a memory facility for storing data, and also data processing instructions to be executed by the data processor,
means for entering into the computer in one single entry-pass, a complete set of data for a given patient, including data which represent the values of hematology parameters, derived from that patient's blood assay;
a central processing unit adapted to process the patient derived data upon entry via the entry means, as well as data stored in the memory facility, the unit including
means for evaluating blood-derived parametric values, and means for ascertaining a clinically important interval (CII) combination applicable to blood-derived parametric values from a listing of plural CII's and producing output messages therefrom;
and a printer connected to the data processor, for printing out the messages of hematology-diagnostic significance, and applicable to that patient;
wherein the memory facility stores a data base, and execution-instructions of an automatically interpreting hematologic/diagnostic system, which is suitable for operation upon the hematology parameters, and their blood-derived values;
the data base including:
a relatively large number of messages of hematologic diagnostic significance, each message being associated with a range of values for each of the hematologic parameters, each range of values constituting one CII, and the messages being adapted for printout;
a listing of the CII's within which the blood-derived parametric values may lie, the listing including a series of consecutive descriptive phrase associated with each CII; and
the stored execution-instructions including directions to the processor, to:
retrieve from the memory facility, and prepare for printout in one single printout pass, a complete set of messages applicable to the given patient, the one or more messages whose range combinations apply to the blood-derived parametric values, and cause the printer to print out the prepared messages in one single printout pass.

11. The apparatus of claim 10 wherein the printout is a human language description of the hematologic condition of said patient.

12. A method of non-interactively interpreting hematology results, comprising:

entering data representing the values of hematology parameters derived from blood into a data processor which includes stored plural messages of hematological diagnostic significance, each message being associated with a range of values for each of a plurality of hematology parameters, and being in a form to permit the interpretation of the hematologic condition applicable to its range, each range of values constituting one clinically important interval (CII) a stored listing of the CII's within which the parametric values may lie, the listing including a series of consecutive CII numbers and a range of values and a descriptive phrase associated with each CII and stored execution instructions which effect evaluation of parametric values and the retrieval of one or more messages whose CII combinations apply to the parametric values;

evaluating the entered data by the stored instructions to retrieve messages applicable to the relevant CII's; and producing the applicable messages in sensible form.

* * * * *